$C_{14}$ PHENYL-SUBSTITUTED DERIVATIVES OF PROSTAGLANDIN ANALOGUES

BACKGROUND OF THE INVENTION

1. Field of the Invention

The compounds of this invention are analogues of natural prostaglandins.

Natural prostaglandins are salicyclic compounds related to prostanoic acid, the structure of which is:

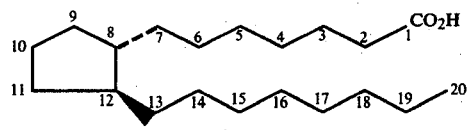

By convention, the carbon atoms of I are numbered sequentially from the carboxylic carbon atom. An important stereochemical feature of I is the trans-orientation of the sidechains $C_1-C_7$ and $C_{13}-C_{20}$, an orientation common to all natural prostaglandins. In I, as elsewhere in this specification, solid lines (—) provide a reference plane (such as the cyclopentyl ring or the bonds among atoms $C_1-C_7$ and $C_{13}-C_{20}$); a dashed line ( - - - ) indicates projection of a covalent bond below such reference plane (alpha-configuration); while a wedged line (▬) represents direction above such plane (beta-configuration). Those conventions apply to all structural formula subsequently discussed in this specification. In some structures, however, a swung dash or serpentine line (∼) denotes orientation of a covalent bond either above or below a plane of reference (indicated by the Greek letter xi in the nomenclature of such structures).

Natural prostaglandins have the general structure,

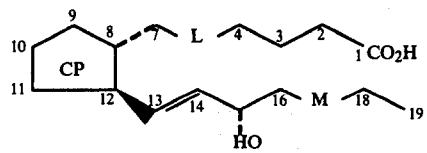

in which: L and M may be ethylene or cis-vinylene radicals; and the cyclopentyl ring

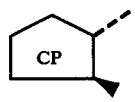

may be:

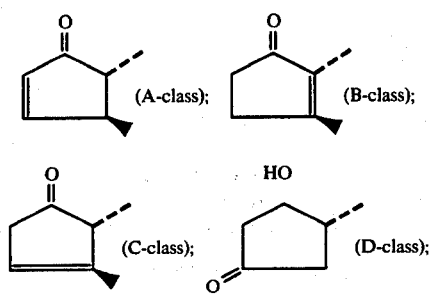

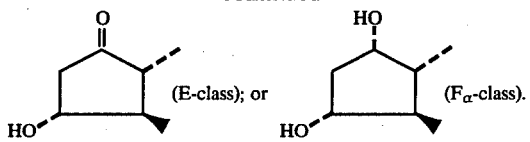

Formula II and all representations of the cyclopentyl moiety depict the nat-isomer, i.e., the $C_7-C_8$ bond in the alpha-configuration and the $C_{12}-C_{13}$ bond in the beta-configuration. In the ent-isomer (which does not occur in nature), the direction on the bonds at $C_7-C_8$ and $C_{12}-C_{13}$ is reversed.

Prostaglandins are classified according to the functional groups present in the five-membered ring and the presence of double bonds in the ring or chains. Prostaglandins of the A-class (PGA or prostaglandin A) are characterized by an oxo group at $C_9$ and a double bond at $C_{10}-C_{11}$ ($\Delta^{10,11}$); those of the B-class (PGB) have an oxo group at $C_9$ and a double bond at $C_8-C_{12}$ ($\Delta^{8,12}$); compounds of the C-class (PGC) contain an oxo group at $C_9$ and a double bond at $C_{11}-C_{12}$ ($\Delta^{11,12}$); members of the D-class (PGD) have an oxo group at $C_{11}$ and an alpha-oriented hydroxy group at $C_9$; prostaglandins of the E-class (PGE) have an oxo group at $C_9$ and an alpha-oriented hydroxyl group at $C_{11}$; and members of the $F_\alpha$-class ($PGF_\alpha$) have an alpha-directed hydroxyl group at $C_9$ and an alpha-oriented hydroxyl group at $C_{11}$. Within each of the A, B, C, D, E, and F classes of prostaglandins are three subclassifications based upon the presence of double bonds in the side-chains at $C_5-C_6$, $C_{13}-C_{14}$, or $C_{17}-C_{18}$. The presence of a trans-unsaturated bond only at $C_{13}-C_{14}$ is indicated by the subscript numeral 1; thus, for example, $PGE_1$ (or prostaglandin $E_1$) denotes a prostaglandin of the E-type (oxo-group at $C_9$ and an alpha-hydroxyl at $C_{11}$) with a trans-double bond at $C_{13}-C_{14}$. The presence of both a trans-double bond at $C_{13}-C_{14}$ and a cis-double bond at $C_5-C_6$ is denoted by the subscript numeral 2; for example, $PGE_2$. Lastly, a trans-double bond at $C_{13}-C_{14}$, a cis-double bond at $C_5-C_6$ and a cis-double bond at $C_{17}-C_{18}$ is indicated by the subscript numeral 3; for example, $PGE_3$. The above notations apply to prostaglandins of the A, B, C, D, and F series as well; however, in the last, the alpha-orientation of the hydroxyl group at $C_9$ is indicated by the subscript Greek letter α after the numerical subscript.

Nomenclature of prostaglandins and their analogues deserves note insofar as there are three current systems followed in the scientific and patent literature. One system for convenience referred to as the Nelson system, uses the trivial names of prostaglandins and designates analogues by modifications of the trivial names (see - J. Med. Chem., 17; 911 [1974]). Another system follows the rules of the International Union of Pure and Applied Chemistry (IUPAC) and refers to prostaglandins and their analogues as derivatives of heptanoic acid. A third system employs a convention of Chemical Abstracts ("CA") that designates prostaglandins and derivatives thereof as derivatives of prostanoic acid. An example of each system is provided below for the following structure:

United States Patent [19]

Buckler et al.

[11] 4,149,007
[45] Apr. 10, 1979

[54] $C_{14}$ PHENYL-SUBSTITUTED DERIVATIVES OF PROSTAGLANDIN ANALOGUES

[75] Inventors: Robert T. Buckler, Edwardsburg, Mich.; David L. Garling, Elkhart, Ind.

[73] Assignee: Miles Laboratories, Inc., Elkhart, Ind.

[21] Appl. No.: 809,786

[22] Filed: Jun. 24, 1977

[51] Int. Cl.$^2$ ............................................ C07C 177/00
[52] U.S. Cl. .................................. 560/53; 560/55; 562/463; 424/308
[58] Field of Search .................. 560/53, 55; 562/463; 260/520; 424/308

Primary Examiner—Paul J. Killos
Attorney, Agent, or Firm—James D. McNeil; Jerome L. Jeffers

[57] ABSTRACT

Analogues of prostaglandins A, E and F in which a phenyl moiety is attached to the $C_{14}$ carbon atom are disclosed. Also disclosed are methods of preparing the analogues and starting materials. The compounds have the structural formula:

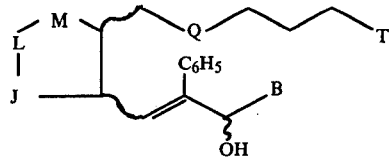

in which J is methylene, R or S-hydroxymethylene or methine; L is methylene or methine and can be methine only when J is methine; M is carbonyl, R or S-hydroxymethylene; Q is ethylene, Z-vinylene or inter-phenylene; T is an alkoxy-carbonyl having from 2 to 3 carbon atoms inclusive, or carboxyl; and B is a loweralkyl of from 1 to 5 carbon atoms.

The prostaglandin analogues of the present invention exhibit a separation of pharmacological activity. The analogues can be used for platelet aggregation (and Methyl 14-Phenyl-11α,15S-dihydroxy-9-oxoprost-13E-en-1-oate can be used for antagonism for smooth muscle stimulation) without the accompanying undesirable side effects of natural prostaglandins, e.g., flush, headache, abdominal cramps and nausea.

34 Claims, No Drawings

(a) $C_{14}$ phenyl-substituted analogues of prostaglandins A, E and F having the structural formula:

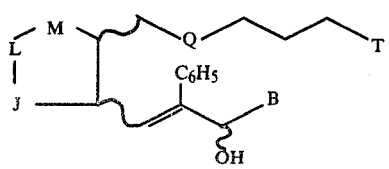

wherein J is methylene, R-hydroxymethylene, S-hydroxymethylene or methine; L is methylene or methine, with the proviso that L is methine only when J is methine; M is carbonyl, R-hydroxymethylene or S-hydroxymethylene; Q is ethylene, Z-vinylene or inter-phenylene; T is an alkoxycarbonyl having from 2 to 3 carbon atoms inclusive, carboxyl, or pharmacologically acceptable, non-toxic salts thereof; and B is a loweralkyl having from 1 to 5 carbon atoms; Included in this genus are the structures shown in IVb - IVg:

(b) $C_{14}$ phenyl-substituted analogues of $PGE_1$ having the structural formula IVb:

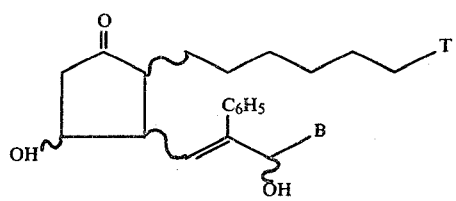

wherein T and B are as defined hereinabove;

(c) $C_{14}$ phenyl-substituted analogues of 11-deoxy-$PGE_1$, having the structural formula IVc:

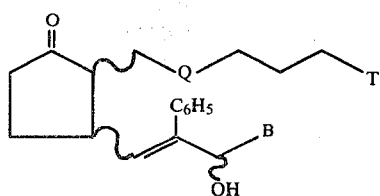

wherein Q is ethylene or inter-phenylene; and T and B are as defined hereinabove;

(d) $C_{14}$ phenyl-substituted analogues of $PGE_2$, having the structural formula IVd:

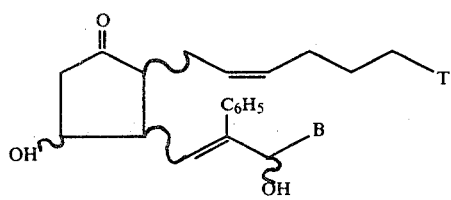

wherein T and B are as defined hereinabove;

(e) $C_{14}$ phenyl-substituted analogues of 11-deoxy-$PGE_2$, having the structural formula IVe:

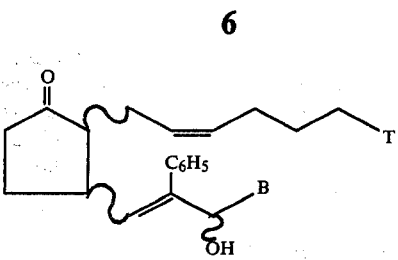

wherein T and B are as defined hereinabove;

(f) $C_{14}$ phenyl-substituted analogues of $PGA_1$, having the structural formula IVf:

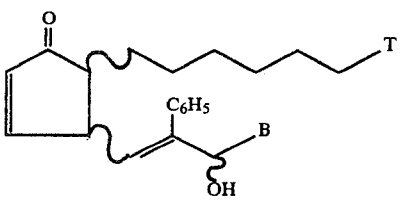

wherein T and B are as defined hereinabove;

(g) $C_{14}$ phenyl-substituted analogues of $PGF_{2\alpha}$, having the structural formula IVg:

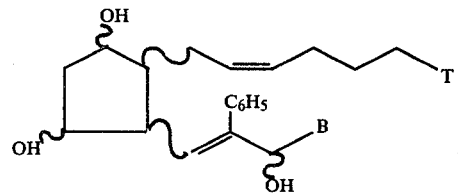

wherein T and B are defined hereinabove;

(h) a therapeutic method of inhibiting platelet aggregation in an individual for whom such therapy is indicated, by administration of a compound having the structural formula IV:

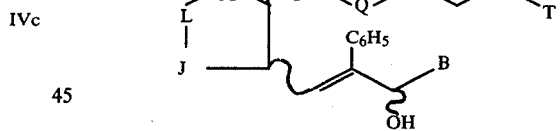

(i) a therapeutic method of inhibiting the smooth muscle stimulant response to $PGE_1$ and $PGF_{2\alpha}$ in an individual for whom such therapy is indicated, by administration of a compound having the structural formula V:

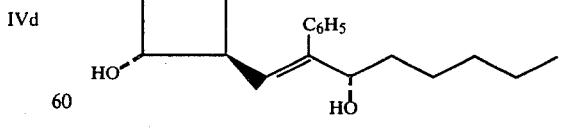

(k) organolithiocuprates having the formula:

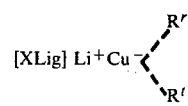

wherein Lig represents a solubilizing ligand. Generally Lig is a tri-(di-alkylamino) phosphine of 6-12 carbon atoms, trialkylphosphine having 3-12 carbon atoms, diarylphosphine, dialkylsulfide having 4-8 carbon atoms, arylsulfide, or di-(trialkylsilyl) amino having 6-12 carbon atoms. Specifically Lig can be a tri-(dimethylamino) phosphine, tri-(n-butyl)phosphine, diphenylphosphine, diisopropylsulfide, dibutylsulfide, phenylsulfide, or di-(trimethylsilyl)amino group.

R$^r$ is iodide, thiophenylate, alkyn-1-yl having 3 to 8 carbon atoms or R$^t$;

R$^t$ is a radical having the formula:

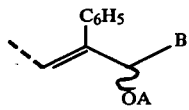

A is an acid-labile hydroxyl-protecting group, generally a tetrahydropyran-2-yl, trialkylsilyl, triarylsilyl, alkoxyalkyl having 2-6 carbon atoms, or a triarylmethyl group; and specifically is tetrahydropyran-2-yl, dimethyl(t-butyl)silyl, dimethylisopropylsilyl, trimethylsilyl, 1-ethoxyethyl, ethoxymethyl, 1-methoxyethyl, methoxymethyl, 2-ethoxyprop-2-yl, 2-methoxyprop-2-yl, or triphenylmethyl; B is a loweralkyl having from 1 to 5 carbon atoms; and X is an integer of the set 1 to 2.

(k) methods of preparing organolithiocuprates having the formula VI:

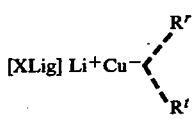

(l) a method of synthesizing a prostaglandin analogue having the structural formula IV:

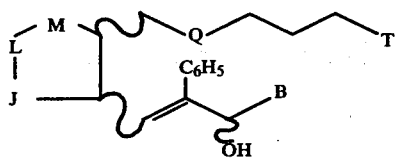

by reacting an organolithiocuprate having the formula VI with a cyclopent-2-en-1-one having the structural formula VIII:

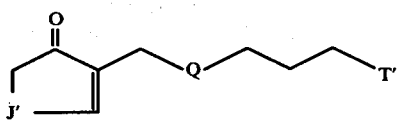

wherein T' is an alkoxycarbonyl having from 2 to 3 carbon atoms inclusive or —CH$_2$OH and wherein J' is methylene or —CH$_2$OA, to form a first intermediate having the structural formula IX:

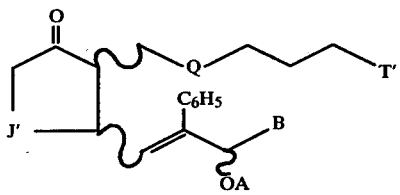

treating IX with a weak acid to obtain a first compound having the structural formula X:

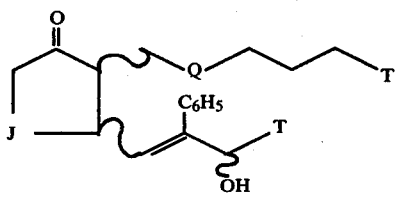

when T is alkoxycarbonyl, hydrolyzing the first compound to obtain a second compound having the structural formula XI:

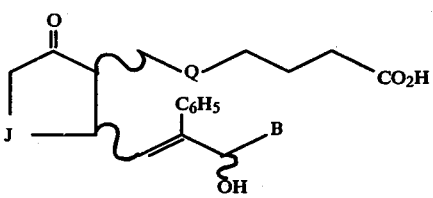

when J is R-hydroxymethylene or S-hydroxymethylene, reducing the first compound to obtain a third compound having the structural formula XII:

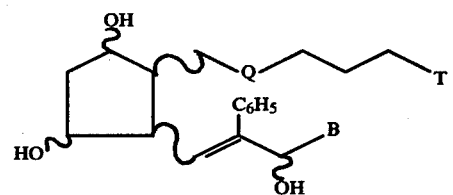

when J is R-hydroxymethylene or S-hydroxymethylene, dehydrating the first compound to obtain a fourth compound having the structural formula XIII:

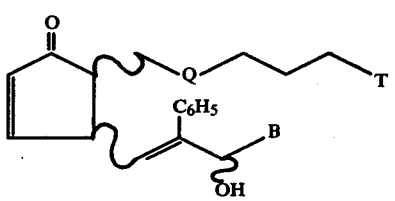

(m) iodovinyl alcohols having the structural formula XIV:

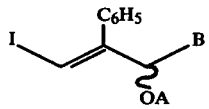

(n) methods of preparing iodovinyl alcohols having the structural formula XIV;

(o) iodovinyl alcohols having the structural formula XV:

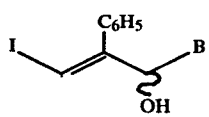

XV; and (p) methods of preparing iodovinyl alcohols having the structural formula XV.

DETAILED DESCRIPTION OF THE INVENTION

The compounds of the present invention, having the formula IV are prepared via the 1,4-conjugate addition of a 2-cyclopenten-1-one and an organolithiocuprate as reported by Sih, et. al., (*J. Amer. Chem. Soc.*, 97:857–865 [1975] and references cited therein). The reaction proceeds in a variety of inert solvent systems of which ether, tetrahydrofuran, hexane, pentane or toluene are representative. The inert atmosphere can be provided by the use of argon or nitrogen. The prostaglandin analogues of formula IV are prepared according to the reaction sequence depicted in Table A, described hereinafter.

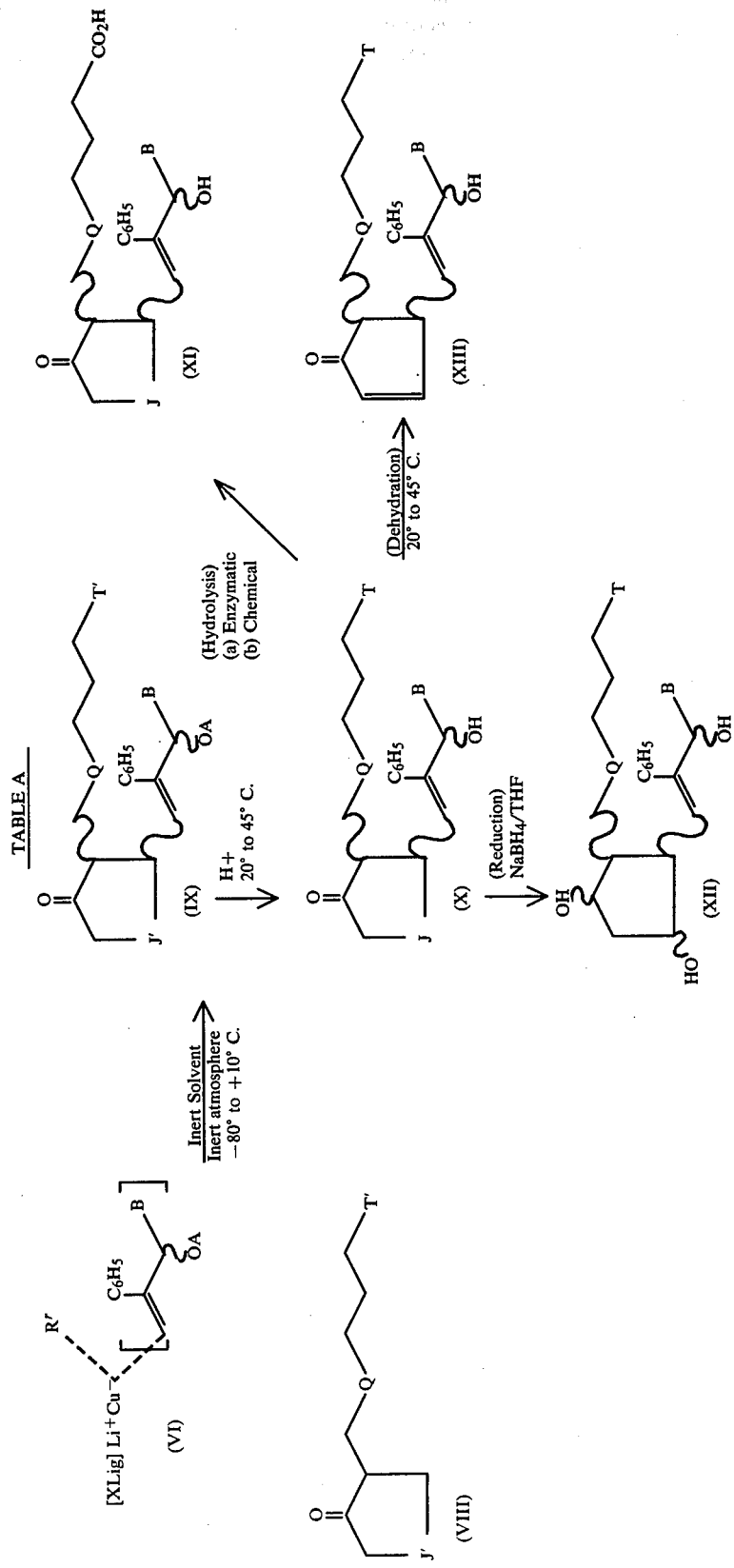

The reaction of the appropriate 2-cyclopenten-1-one having the structural formula VIII:

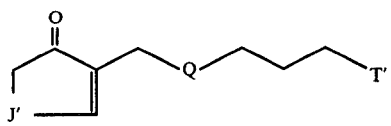
(VIII)

with the organolithiocuprate of formula VI:

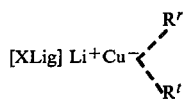

in an inert solvent, under an inert atmosphere at a temperature of from −80° to +10° C. for about 0.25 to 3 hours provides the intermediate having the structural formula IX:

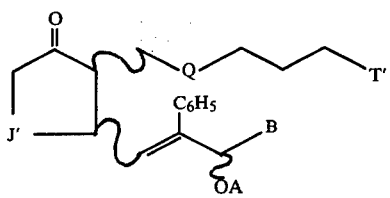
(IX)

Hydrolysis of the intermediate IX provides compound XI. Chemical hydrolysis can be accomplished by treatment with alcoholic KOH, e.g. 5% KOH in 3:1 methanol:water. Alternatively, chemical hydrolysis can be accomplished by treatment with a weakly-acidic water mixture, e.g., acetic acid-water (65:35 VV) with 10% tetrahydrofuran, at a temperature of about 20° C. to 45° C. for about 0.5 to 48 hours. Enzyme hydrolysis can be accomplished by treatment with hog pancreatic lipase.

Dehydration of Compound X, where J is R or S-hydroxymethylene, with a weakly-acid water mixture, such as acetic acid-water, under an inert atmosphere, at a temperature of about 50° to 80° C. (described in *J. Org. Chem.*, 34: 3552 [1969]) provides Compound XIII.

Reduction of Compound X with sodium borohydride in tetrahydrofuran or other suitable polar solvent provides Compound XII (See *J. Org. Chem.*, 34: 3552 [1969]).

Non-toxic, pharmacologically acceptable salts of Compound IV can be prepared by neutralization of III, where T is carboxyl, with an equivalent or excess amount of the corresponding non-toxic salt-forming organic or inorganic base. The salts are prepared by procedures well known in the art. Suitable salts include sodium, potassium, ammonium and the like. The salts may be isolated by lyophilization of the resulting mixture, or by filtration if sufficiently insoluble, or by similar well-known techniques.

All compounds of this invention can be isolated from reaction mixtures and purified by well-known organic chemistry procedures. For example, the compounds can be isolated by dilution of the reaction mixture with water, extraction with a water-immiscible solvent such as benzene, cyclohexane, ether, ethyl acetate, methylene chloride, toluene and the like; chromatography; distillation or a combination of these procedures. Purification of these compounds can be accomplished by methods which are well-known in the art for the purification of prostaglandins, lipids, fatty acids, and fatty esters. Such methods as reverse phase partition chromatography; counter-current distribution; adsorption chromatography on acid washed magnesium silicate, neutral or acid washed silica gel, alumina or silicic acid; preparative paper chromatography; preparative thin layer chromatography; high pressure liquid-liquid chromatography; gas-liquid chromatography; and combinations thereof can be used to purify the compounds produced by the processes of this invention.

Preparation of Organolithiocuprates

The organolithiocuprate utilized in the reaction is prepared in solution prior to reaction with the 2-cyclopenten-1-one, and is represented by formula VI:

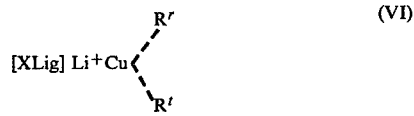
(VI)

The organolithiocuprate is prepared from the iodovinyl alcohol of structure XIV. In turn, the iodovinyl alcohol of structure XIV is prepared from the appropriate ketone via an enol tosylate route.

As depicted in Table B and described in detail following Table B, the appropriate ketone XVI is converted to a formyl ketone and treated with p-toluene sulfonyl chloride to give the corresponding enol tosylate XIX. The enol tosylate is converted to the iodovinyl ketone XX, which is then reduced to the iodovinyl alcohol XIX.

The iodovinyl alcohol is reacted with ethyl vinyl ether or methyl isopropenyl ether to give a mixed acetal (XXII). The mixed acetal is then lithiated with t-butylithium and reacted with a solubilizing Lig complex of copper n-propyl acetylide to yield the desired organolithicuprate VI.

TABLE B

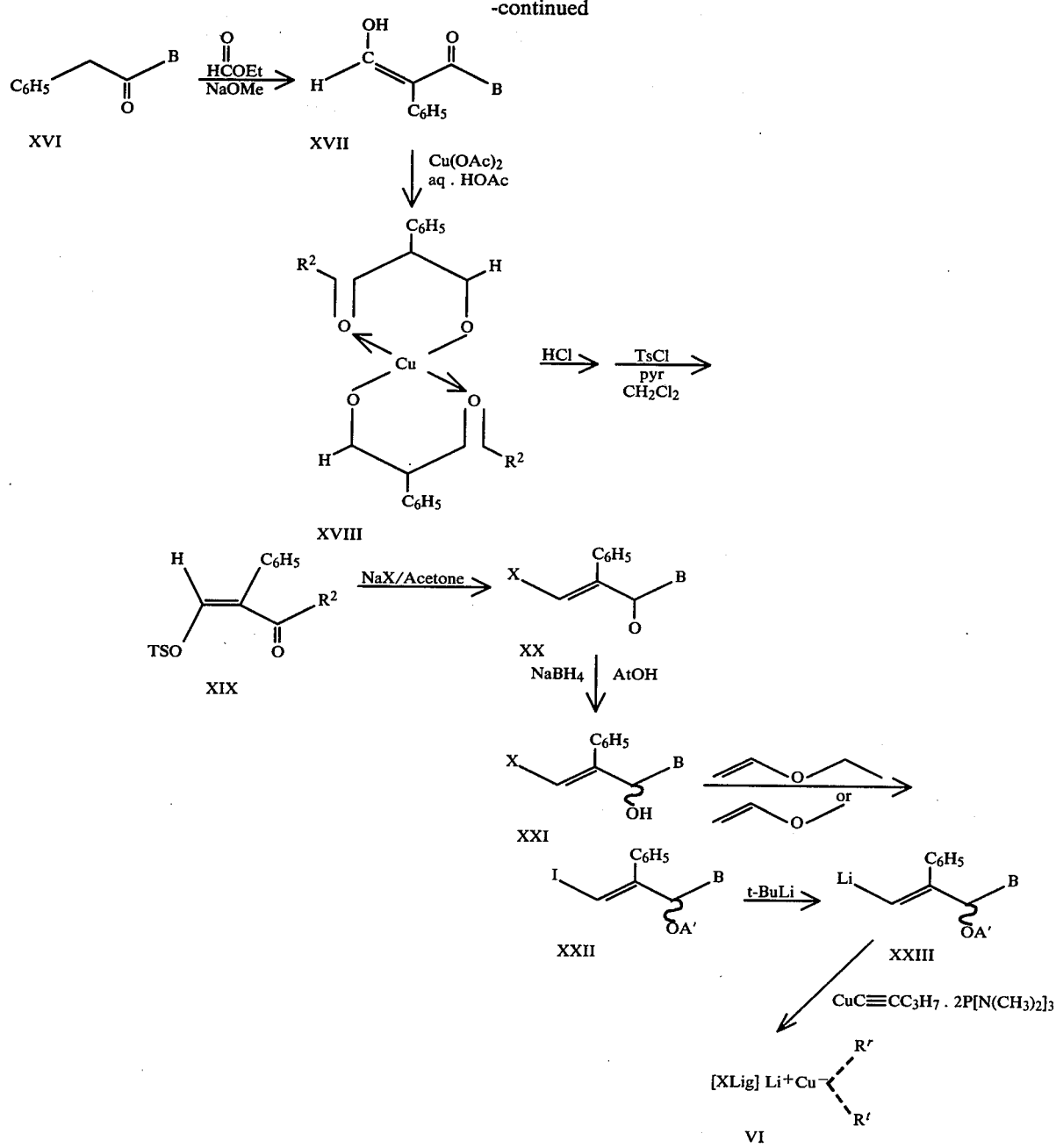

Preparation of Iodovinylalcohol and Organolithiocuprate

As shown in Table B, the appropriate ketone XVI is treated with ethyl formate under basic conditions to give the formyl ketone XVII which is isolated and purified as the copper chelate XVIII. The ketone XVII is regenerated by treatment with acid, quickly extracted, and immediately treated with p-toluene-sulfonyl chloride in the presence of a tertiary amine such as pyridine, to give the enol tosylate XIX. Halogeno displacement, by treatment with a halogen salt such as sodium iodide, produces the iodo ketone XX, which is directlly reduced to the iodovinyl alcohol XXI using sodium borohydride. When B of the iodovinyl alcohol XXI is n-pentyl, the alcohol is not readily resolved and consequently is utilized as the racemate. The novel iodovinyl alcohols have utility as intermediates in producing the prostaglandin analogues of the present invention.

The iodovinyl alcohol XXI is reacted with ethyl vinyl ether or methyl isopropenyl ether to give a mixed acetal having a hydroxy-protecting group A' XXII where A' is $CH(CH_3)OC_2H_5$ or $—C(CH_3)_2OCH_3$. The acetal XXII is lithiated with metallic lithium or an alkyl-lithium (n-butyl, sec-butyl or tert-butyl) to form the lithio complex XXIII. The lithio complex XXIII is reacted with the solubilizing Lig, for example, the hexamethylphosphorous triamide complex of copper n-propyl acetylide, to produce the desired organolithiocuprate VI. Specifically, (hexamethylphosphorous triamide)$_2$-copper pentyne is disclosed in J. Amer. Chem. Soc., 94: 7211 (1972 and in J. Org. Chem., 31: 4071 (1966). Tri-n-butylphosphine-copper-(I)iodide is described in

*Inorg. Synth*, 7: 9 (1963). Hexamethylphosphorous triamide-copper(I) iodide is taught in *Prostaglandins*, 7: 38 (1974). Preparation of phenylthio-copper is disclosed in *Synthesis*, 602 (1974). For a thorough review of organolithiocuprates and their utility in the synthesis of natural prostaglandins, refer to *J. Amer. Chem. Soc.* 97: 857 and 865 (1975). The novel organolithiocuprates have utility as intermediates in producing the prostaglandin analogues of the present invention.

When B of the ketone XVI is methyl, the ketone is phenylacetone, commercially available from Aldrich Chemical Co., Milwaukee, Wisconsin. When B is n-pentyl, the ketone is 1-phenyl-2-heptanone, which can be prepared as described in *J. Chem. Eng. Data*, 15, 200 (1970).

The organolithiocuprate is reacted with the desired 2-cyclopenten-1-one of formula VIII is depicted earlier in Table A. The 2-cyclopenten-1-ones employed in the synthesis include: (Example 1) 2(6-carbomethyoxyhexyl)-4R-hydroxy-2-cyclopenten-1-one; (Example 4) 2[2-(3-carbomethoxypropyl)-benzyl]2-cyclopenten-1-one; (Example 5) 2-(6-carbomethoxyhexyl)-2-cyclopenten-1-one; (Example 7) 2-(6-carboethoxy-2Z-hexenyl)-4R-hydroxy-2-cyclopenten-1-one; (Example 8) 2-(6-carbomethoxy-2Z-hexenyl)-2-cyclopenten-1-one. The synthesis of these 2-cyclopenten-1-ones is described in *J. Amer. Chem. Soc.*, 95: 1676 (1973), and *Tetrahedron Letters*, No. 25, 2313 (1973).

The starting 2-cyclopenten-1-one of Example 4 is prepared from the dione XXIV

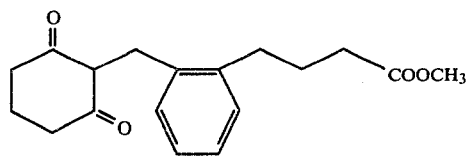

by converting the dione to the chlorodione XXIV

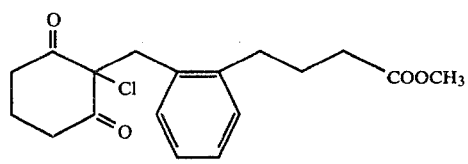

which can be rearranged to the unsaturated inter-o-phenylene of formula VIII.

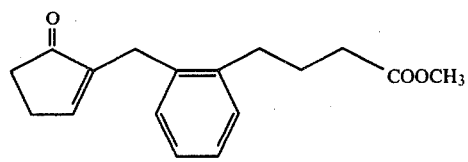

See *J. Org. Chem*, 36:2021 (1971).

The following Table C illustrates preferred embodiments of the prostaglandin analogues of the present invention compiled by Example No. and Compound No. and identified by the Chemical Abstracts system of nomenclature.

TABLE C

| Example Number | Compound Number | Chemical Abstracts Nomenclature |
|---|---|---|
| 1 | TR 4412 | Methyl 14-Phenyl-11α,15S-dihydroxy-9-oxoprost-13E-en-1-oate |
| 2 | TR 4478 | 14-Phenyl-11α,15S-dihydroxy-9-oxoprost-13E-en-1-oic acid |
| 3 | TR 4477 | 14-Phenyl-11α,15R-dihydroxy-9-oxoprost-13E-en-1-oic acid |
| 4 | TR 4298 | Methyl 5,6,17,18,19,20-hexanor-4,7-inter-o-phenylene-14-phenyl-15S-hydroxy-9-oxo-ent-prost-13E-en-1-oate |
| 5 | TR 4547 | Methyl dl-14-phenyl-15R,S-hydroxy-9-oxoprost-13E-en-1-oate |
| 6 | TR 4556 | Methyl dl-14-phenyl-15R,S-hydroxy-9-oxoprost-13E-en-1-oic acid |
| 7A | TR 4613 | Ethyl 14-Phenyl-11α,15R-dihydroxy-9-oxoprosta-5Z,13E-dien-1-oate |
| 7B | TR 4614 | Ethyl-14-Phenyl-11α,15S-dihydroxy-9-oxoprosta-5Z,13E-dien-1-oate |
| 8 | TR 4545 | Methyl dl-14-phenyl-15R-hydroxy-9-oxoprosta-5,13E-dien-1-oate |
| 9 | TR 4546 | Methyl dl-14-phenyl-15S-hydroxy-9-oxoprosta-5Z,13E-dien-1-oate |
| 10 | TR 4578 | dl-14-Phenyl-15S-hydroxy-9-oxoprosta-5Z,13E-dien-1-oic acid |
| 11 | TR 4599 | dl-14-Phenyl-15R-hydroxy-9-oxoprosta-5Z,13E-dien-1-oic acid |
| 12 | TR 4505 | 14-Phenyl-15R-hydroxy-9-oxo-ent-prosta-10,13E-dien-1-oic acid |
| 13 | TR 4514 | 14-Phenyl-15S-hydroxy-9-oxoprosta-10,13E-dien-1-oic acid |
| 14 | TR 4666 | 14-Phenyl-9α,11α,15R,S-trihydroxyprosta-5Z,13E-dien-1-oic acid |

The compounds represented by Formula IV inhibit aggregation of human platelets in vitro as demonstrated hereinafter. In comparison, only $PGE_1$ of the natural prostaglandin displays similar activity. In addition, TR 4412 (Example 1), exhibited antagonism to the smooth muscle stimulant effects of $PGE_1$ and $PGF_{2\alpha}$. In contrast to the natural prostaglandins, the prostaglandin analogues of the present invention exhibit specific pharmacological properties, i.e., have a separation of activity. Thus the analogues can be used for platelet aggregation (and TR 4412 for antagonism to smooth muscle stimulation) without accompanying undesirable side-effects, e.g., flush, headache, abdominal cramps and nausea.

DESCRIPTION OF THE PREFERRED EMBODIMENTS

Examples 1, 2 and 3 illustrate the preparation of prostaglandin $E_1$ analogues of the present invention.

EXAMPLE 1

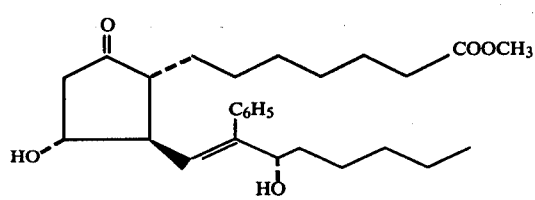

Methyl 14-Phenyl-11α,15S-dihydroxy-9-oxoprost-13E-en-1-oate

The reaction pathway is shown below:

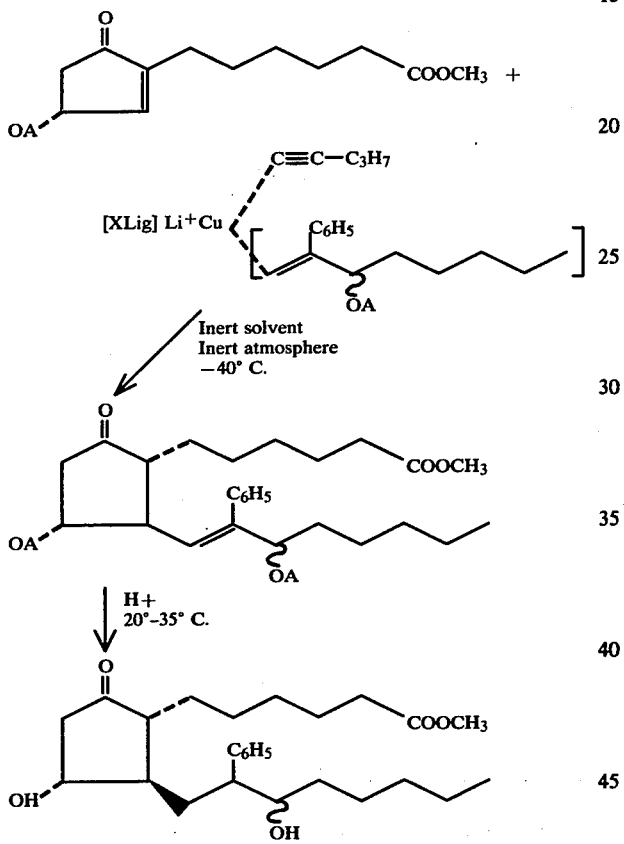

A. Preparation of Iodovinylalcohol [(E)-1-Iodo-2-phenyl-1-octen-3-ol]

An 84 g (0.47 mole) portion of 1-phenyl-2-heptanone and a 52 g (0.7 mole) portion of ethyl formate were combined and added at once to a slurry of sodium methoxide [freshly prepared from 11 g (0.48 gram atoms) of sodium and 25 ml MeOH] in 200 ml dry tetrahydrofuran. Other formates, e.g., methyl, are suitable.

After four hours stirring at room temperature, the mixture was purified by being dissolved in water and poured into a solution of 75 g cupric acetate and 31 ml acetic acid in 1500 ml water. The copper salt of the chelate was separated as a viscous oil, taken up in chloroform and dried over MgSO₄. Removal of the chloroform left an oil which crystallized overnight. A 96 g (0.2 mole) portion of the copper salt was slurried with 35 ml concentrated HCl and methylene chloride in 200 water. The organic phase was separated, dried, and the solvent removed to give a yellow oil which was taken up in 300 ml methylene chloride and 38 ml pyridine and treated dropwise at 0° with a solution of 76 g (0.4 mole) p-toluenesulfonyl chloride (tosyl chloride) and 26 ml pyridine in 150 ml methylene chloride. Other suitable solvents include benzene. After stirring overnight at 0°, the reaction mixture was washed with cold water, dried and the solvent removed to yield an oil which was purified by chromatographic techniques to yield 43 g of the enol tosylate. The enol tosylate was stirred overnight with a 52 g (0.3 mole) portion of sodium iodide in 500 ml dry acetone, the mixture poured into water, extracted with benzene and dried. Solvent removal left an oil which was added to a slurry of a 5 g (0.13 mole) portion of sodium borohydride in 300 ml absolute ethanol at 0°. After 4 hours stirring at room temperature, the reduction was quenched using 12 ml acetic acid in 500 ml water. Extraction with benzene, washing with bicarbonate, drying over MgSO₄, and solvent removal gave 34.5 g (0.105 mole) of (E)-1-Iodo-2-phenyl-1-octen-3-ol as an oil, 22.3% yield. Calculated for $C_{14}H_{19}IO$: C, 50.92; H, 5.80; Found: C, 51.29; H, 5.96.

B. Preparation of Organolithiocuprate from Iodovinylalcohol Lithium [1-pentynyl,3RS[2-(2-methoxy)-propoxy]-2-Phenyl-1E-octenyl-1]cuprate The hydroxyl function of a 3.8 g (12 mmol) portion of (E)-1-iodo-2-phenyl-1-octen-3-ol was protected by dissolving the alcohol in 16 ml methyl isopropenyl ether, adding 5 drops of dichloroacetic acid and stirring. Protection of the hydroxyl group was determined by examination of the infrared spectra; after absence of hydroxyl stretching bands was determined, the reaction was neutralized by the addition of 10 drops of Et₃N and the solvent removed on a rotary evaporator at 35°. The protected alcohol, dissolved in 5 ml dry ether, was added dropwise to 20 ml of a solution of t-butyllithium (1.4 M in pentane; −78°) under an argon atmosphere. The temperature was maintained at approximately −60° during the addition; the mixture was then stirred for an additional hour at a temperature of −40°. After stirring was completed, a solution of 2.62 g [20 mmol] cuprous-n-propylacetylide solubilized with 8 ml hexamethylphosphrous triamide in 5 ml dry ether was pumped in slowly to form the desired lithiocuprate reagent. The lithiocuprate reagent was stirred for an additional hour at −40°.

C. Preparation of 2-Cyclopenten-1-one

The hydroxyl function of a 2 g (8 mmol) portion of 4-hydroxy-(6-carbomethoxy-2-hexanyl)-2-cyclopenten-1-one was protected by dissolving the cyclopentenone in 8 ml methyl isopropenyl ether, adding 5 drops of dicholoracetic acid and stirring the solution overnight. Protection of the hydroxyl group on the cyclopentenone ring was determined by examination of infrared spectra; after absence of hydroxyl stretching bands was determined, the reaction was neutralized by the addition of 10 drops of Et₃N and the solvent removed on a rotary evaporator at 35°.

The synthesis of the prostaglandin E₁ analogue was achieved as described below.

The protected cyclopentenone was then dissolved in 5 ml dry ether and added all at once to the lithiocuprate reagent. The reaction mixture was stirred at −40° for 3 hours, warmed to room temperature and quenched by pouring into 300 ml 1 M ammonium sulfate. After stirring for 45 minutes the layers were separated and the aqueous layer was extracted twice with 200 ml portions of ether. The combined ether extracts were stirred with 250 ml cold H₂SO₄ (5%), filtered through dicalite to break the emulsion and the layers separated. The organic layer was washed with brine to neutrality, the solvent removed and the oil stirred for 1½ hours at room temperature in aqueous acetic acid (60%). The solution was azeotroped with toluene on a rotary at room temperature. The resultant oil was purified by chromatographic techniques on 150 g SG-60 using benzene-ethyl acetate (9:1) gradient elution to yield 1115 mg of a mixture of the natural (nat) isomer and its 15-epimer. The mixture was separated by column chromatography eluting with benzene and ethyl acetate gradients. The first-eluted isomer was assigned the structure of the 15-epi isomer, and the second eluted one the nat isomer, on the basis of the known chromatographic behavior of the natural prostaglandin analogues.

The nat isomer, Compound TR 4412, had the following spectral properties:

Analysis—NMR(CDCl₃): δ 3.7(3H,s); δ 4.2(2H,m); δ 7.3(5H,m).

Mass Spectrum (70eV)m/e: 426 (M+—H₂O).

The PGE, 11-deoxy-E, A and F esters can be hydrolyzed to the corresponding acids using methanolic potassium hydroxide or hog lipase, for example hog pancreatic or hog liver lipase. The enzymatic method is preferred when the cyclopentenone ring contains a hydroxyl group to avoid dehydration of the E analogs. Optimization of reaction conditions produces nearly quantitative yields.

Example 2 describes the enzymatic hydrolysis of the nat-PGE₁ methyl ester of Example 1 to its corresponding acid.

EXAMPLE 2

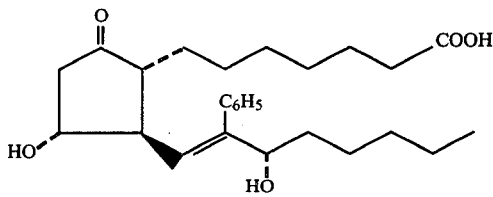

14-Phenyl-11α,15S-dihydroxy-9-oxoprost-13E-en-1-oic acid

A 27 mg portion of hog pancreatic lipase was dissolved in 200 ml of phosphate buffer (pH 7.5) prepared by mixing 32 ml 0.2 M NaH₂PO₄ with 168 ml 0.2 M Na₂HPO₄. A 200 mg portion (0.45 mmol) of the nat-prostaglandin E₁ analogue of Example 1 was dissolved in 7 ml ethanol and added to the buffered lipase solution. The mixture remained cloudy after stirring for 5 hours at 35° C. An additional 27 mg of lipase was added and stirring continued for one hour to produce a clear mixture. The mixture was acidified with 2% H₂SO₄ while being partitioned between ether/water. The ether layer was separated and the aqueous layer extracted several times with ether. The ether layers were combined, washed to neutrality with brine, dried over MgSO₄ and filtered. The solvent was removed in vacuo to yield a yellow oil. The oil was purified by chromatography on 30 g SG-60 using benzene-ethanol (19:1) gradient solution. 100 mg of the starting ester and 75 mg (0.10 mmol) of the desired prostaglandin acid analogue were obtained.

Compound TR 4478 had the following spectral properties:

Analysis—NMR(CDCl₃): δ 4.3(2H,m); δ 5.2(3H,m); δ 5.6(1H,m); δ 7.2(5H,m).

Mass Spectrum (70eV)m/e: 412 (M+—H₂O).

EXAMPLE 3

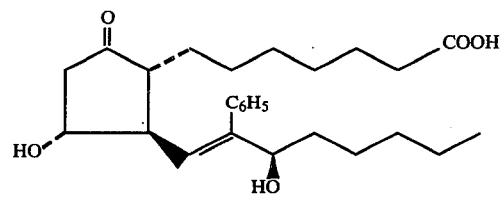

14-phenyl-11α,15R-dihydroxy-9-oxoprost-13E-en-1-oic acid

The method described in Example 2 was used to prepare TR 4477 from the 15-epi methyl ester of Example 1.

Compound TR 4477 had the following spectral properties:

Analysis—NMR(CDCL₃): δ 4.0(1H,m); δ 4.4(1H,m); δ 5.6(1H,m); δ 5.7;1 (3H,s); δ 7.3(5H,m).

Mass Spectrum (70eV)m/e: 412 (M+—H₂O).

Examples 4–6 illustrate the preparation of 11-deoxy prostaglandin E₁ analogues of the present invention.

EXAMPLE 4

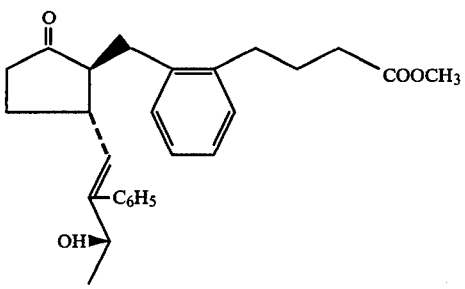

Methyl 5,6,17,18,19,20-hexanor-4,7,-inter-o-phenylene-14-phenyl-15S-hydroxy-9-oxo-ent-prost-13E-en-1-oate The method described in Example 1 was used to prepare TR 4298 by replacing the cyclopentenone with an inter-o-phenylene;

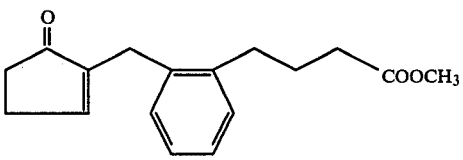

and the organolithiocuprate with

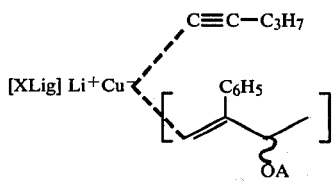

The inter-meta and inter-para analogs can be prepared by substituting the appropriate corresponding inter-phenylene.

Since the cyclopentenone does not contain a hydroxyl group, it was not necessary to "block" the hydroxyl group.

Compound TR 4298 had the following spectral properties:

Analysis—NMR(CDCl$_3$): δ 3.6(3H,s); δ 4.1(1H,m); δ 7.1(9H,m).

Mass Spectrum (70eV)m/e: 402 (M+—H$_2$O).

EXAMPLE 5

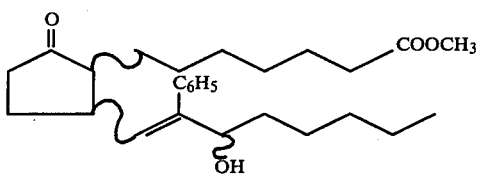

Methyl dl-14-phenyl-15R,S-hydroxy-9-oxoprost-13E-en-1-oate

Repeating in a similar manner the procedure of Example III, but replacing the cyclopentenone with 2-(6-carbomethoxyhexyl)-2-cyclopenten-1-one, yields the prostaglandin analogue mixture shown above.

The mixture had the following spectral properties.

Analysis—NMR(CDCl$_3$): δ 3.6(3H,s); δ 4.2(1H,m); δ 5.4(1H,m); δ 7.2(5H,s).

Mass Spectrum (70eV)m/e: 410 (M+—H$_2$O).

Example 6 illustrates the preparation of an 11-deoxy prostaglandin E$_1$ acid analogue by chemical hydrolysis of its corresponding ester.

EXAMPLE 6

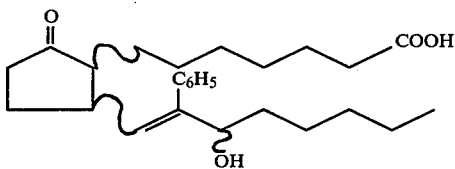

Methyl dl-14-phenyl-15R,S-hydroxy-9-oxoprost-13E-en-1-oic acid

The corresponding deoxy-nat-14-phenyl PGE$_1$ ethyl ester and its 15-epimer were prepared by a procedure similar to that described in Example 4.

A 700 mg (0.44 mmol) portion of the ethyl ester mixture was dissolved in 6 ml methanol to which was added 18 ml of 5% KOH in 3:1 methanol:water and stirred under an inert atmosphere for about 1½ hours. The solvent was removed by evaporation in vacuo, and the residue partitioned between ether and water while being acidified (pH=4) with 2% H$_2$SO$_4$. The layers were separated and the aqueous phase extracted several times with ether. The ether layers were combined, washed to neutrality with brine and dried over MgSO$_4$. The dried material was filtered and the solvent removed in vacuo to yield a yellow oil. The oil was purified by chromatography on 45 g SG-60 using benzene-ethanol (19:1) to yield 131 mg of a mixture of the desired acid analogues.

The mixture had the following spectral properties:

Analysis—NMR(CDCl$_3$): δ 4.3(1H,m); δ 5.6(1H,m): δ 5.9(2H,s); δ 7.2(5H,m).

Mass Spectrum (70eV)m/e: 396 (M+—H$_2$O).

Example 7 illustrates the preparation of prostaglandin E$_2$ analogues of the present invention.

EXAMPLE 7

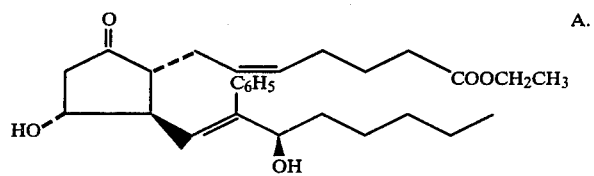

Ethyl 14-Phenyl-11α,15R-dihydroxy-9-oxoprosta-5Z,13E-dien-1-oate

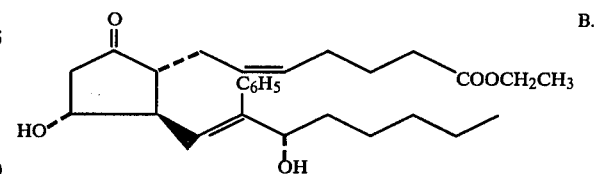

Ethyl-14-Phenyl-11α,15S-dihydroxy-9-oxoprosta-5Z-13E-dien-1-oate

The method described in Example 1 was used to prepare TR 4613 and 4614 by replacing the cyclopentenone with 2-(6-carboethoxy-2Z-hexenyl)-4R-hydroxy-2-cyclopenten-1-one. The mixture was separated by column chromatography.

The compounds had the following spectral properties.

A. Compound TR 4613

Analysis—NMR(CDCl$_3$): δ 4.0(2H,q); δ 5.3(3H,m); δ 7.2(5H,m).

Mass Spectrum (70eV)m/e: 438 (M+—H$_2$O).

B. Compound TR 4614

Analysis—NMR(CDCl$_3$): δ 4.0(2H,q); δ 5.3(3H,m); δ 7.2(5H,m).

Mass Spectrum (70eV)m/e: 438 (M+—H$_2$O).

Examples 8–11 illustrate the preparation of 11-deoxy prostaglandin E$_2$ analogues of the present invention.

EXAMPLE 8

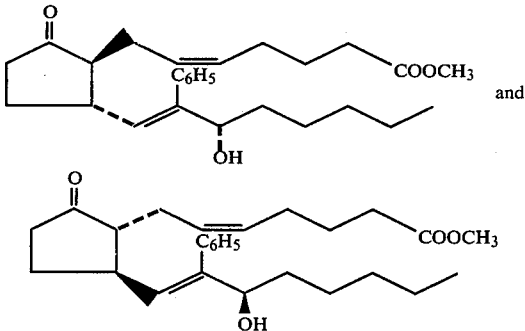

Methyl dl-14-phenyl-15R-hydroxy-9-oxoprosta-5,13E-dien-1-oate

The method described in Example 1 was used to prepare TR 4545 by replacing the cyclopentenone with 2-(6-carbomethoxy-2Z-hexenyl)-2-cyclopenten-1-one.

Since the cyclopentenone does not contain a hydroxyl group, it was not necessary to "block" the hydroxyl group.

The isomeric mixture was not resolved; the mixture had the following spectral properties:

Analysis: NMR(CDCl$_3$): δ 3.6(3H,s); δ 4.2(1H,m); δ 5.4(3H,m); δ 7.2(5H,m).

Mass Spectrum (70 eV)m/e: 408 (M+—H₂O).

EXAMPLE 9

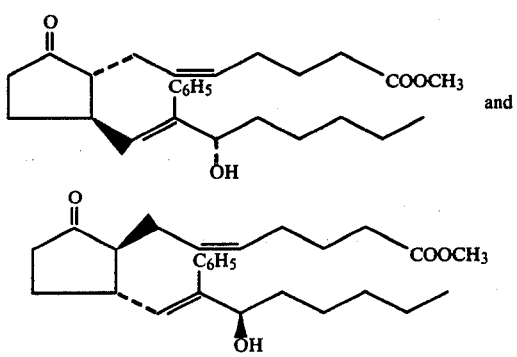

Methyl dl-14-phenyl-15S-hydroxy-9-oxoprosta-5Z,13E-dien-1-oate

The method described in Example 1 was used to prepare TR 4546 by replacing the cyclopentenone with 2-(6-carbomethoxy-2Z-hexenyl)-2-cyclopenten-1-one.

The isomeric mixture was not resolved; the mixture had the following spectral properties.

Analysis: NMR(CCl₄): δ 3.6(3H,s); δ 4.2(1H,m); δ 5.4(3H,m); δ 7.2(5H,m).

Mass Spectrum (70eV)m/e: 408 (M+—H₂O).

EXAMPLE 10

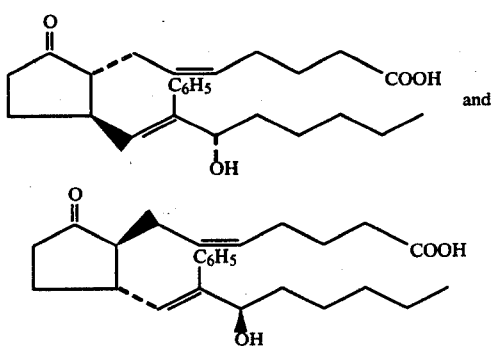

dl-14-Phenyl-15S-hydroxy-9-oxoprosta-5Z,13E-dien-1-oic acid

The chemical hydrolysis method described in Example 6 was used to prepare the acid mixture, TR 4578, from the corresponding methyl ester mixture of Example 9.

The isomeric mixture was not resolved; the mixture had the following spectral properties.

Analysis: NMR(CDCl₃): δ 4.3(1H,m); δ 5.4(3H,m); δ 6.2(2H,m); δ 7.2(5H,m).

Mass Spectrum (70eV)m/e: 394 (M+—H₂O).

EXAMPLE 11

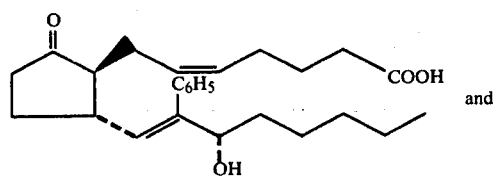

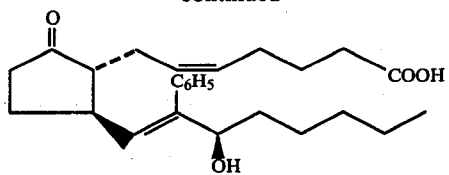

dl-14-Phenyl-15R-hydroxy-9-oxoprosta-5Z-13E-dien-1-oic acid

The chemical hydrolysis method described in Example 6 was used to prepare the acid mixture TR 4599, from the corresponding methyl ester mixture of Example 8.

The isomeric mixture was not resolved; the mixture had the following spectral properties.

Analysis: NMR(CDCl₃): δ 4.3(1H,m); δ 5.4(3H,m); δ 5.6(2H,m); δ 7.2(5H,m).

Mass Spectrum (70eV)m/e: 394 (M+—H₂O).

Examples 12 and 13 illustrate the preparation of prostaglandin A₁ analogues of the present invention by dehydration of the corresponding E₁ analogues.

EXAMPLE 12

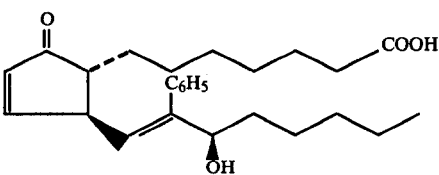

14-Phenyl-15R-hydroxy-9-oxo-ent-prosta-10,13E-dienloic acid

A 125 mg (0.3 mmol) portion of the prostaglandin E₁ analogue of Example 3 (14-Phenyl-11α,15R-dihydroxy-9-oxoprost-10,13E-dien-1-oic acid) was stirred into 10 ml of acetic acid-water (2:1) at 50° C. under an inert atmosphere. Progress of the reaction was followed by thin layer chromatography. After 48 hours, the reaction mixture was extracted with ether. Ether layers obtained were combined and washed to neutrality with brine. Removal of the solvent yielded a yellow oil. The oil was azeotroped with toluene and chromatographed on 70 g SG-60, and eluted with benzene-ethanol (19:1) to yield 102 mg of the PGA₁ analogue.

Compound, TR 4505 had the following spectral properties.

Analysis—NMR(CDCl₃): δ 4.3(1H,m); δ 5.4(2H,m); δ 6.1(1H,m); δ 7.3(6H,m).

Mass Spectrum (70eV)m/e: 394 (M+—H₂O).

EXAMPLE 13

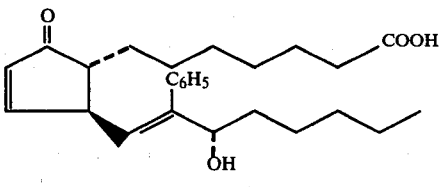

14-Phenyl-15S-hydroxy-9-oxoprosta-10,13E-dien-1-oic acid

Repeating in a similar manner the procedure of Example 12 but replacing the PGE₁ analogue with the analogue prepared in Example 2 (14-Phenyl-11α,15S- dihydroxy-9-oxoprost-13E-en-1-oic acid) yields the above analogue.

Compound TR 4514 had the following spectral properties:

Analysis—NMR(CDCl$_3$); δ 5.0(2H,m); δ 6.0(1H,m); δ 7.2(6H,m).

Mass Spectrum (70eV)m/e: 394 (M+—H$_2$O).

Example 14 illustrates the preparation of a prostaglandin F$_{2\alpha}$ analogue of the present invention.

EXAMPLE 14

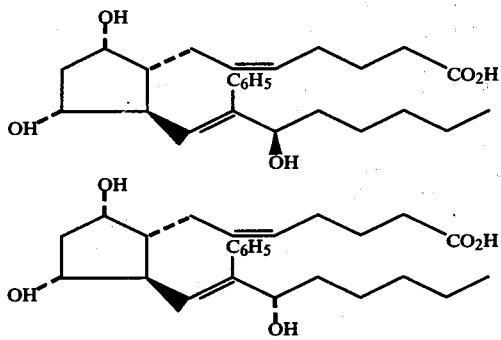

14-Phenyl-7α,11α,15R,S-trihydroxyprosta-5Z,13E-dien-1-oic acid

A 900 mg (2 mmol) portion of the prostaglandin E$_2$ mixture of Example 7A (ethyl 14-Phenyl-11α,15R-dihydroxy-9-oxoprosta-5Z,13E-diene-1-oate and the 15S isomer of 7B) was dissolved in 10 ml dry tetrahydrofuran (THF) and cooled —60 under an inert atmosphere. A total amount of 5 ml of a 0.5 M solution of lithium perhydro-9b-borophenylhydride in tetrahydrofuran was added dropwise, with stirring, over a 5 minute period.

The reaction was allowed to proceed for 4 hours and stirred for 16 hours at —60° C. The reaction was then quenched with 5 ml water, allowed to warm to room temperature, and partitioned between 100 ml ether/100 ml water. The aqueous phase was extracted twice with 100 ml portions of benzene. The combined organic layers (ether and benzene) were washed twice with 50 ml portions of brine, dried over MgSO$_4$, filtered and solvent removed in vacuo to yield a yellow oil. The oil was purified by chromatography on 50 g SG-60, using gradient elution (1:1 EtOAC:C$_6$H$_6$ t 3:1 EtOAC:C$_6$H$_6$) to yield 300 mg (0.66 mmol) of a mixture of the PGF$_{2\alpha}$ ester analogues. The ester analogue mixture was subjected to chemical hydrolysis as described in Example 10, to produce the corresponding acid.

The acid mixture had the following spectral properties:

Analysis—NMR(CDCl$_3$); δ 5.4(3H,m); δ 7.2(5H,m).

Mass Spectrum (70eV)m/e: 412 (M+—H$_2$O).

Compounds of this invention were screened to detect the following biological activities:

(A) effects on the rat stomach, rat colon, chick rectum, and rabbit aorta in vitro (cascade assay);
(B) effect on the rat uterus in vitro;
(C) effect on the guinea pig trachea in vitro;
(D) antagonism of the effects of PGE$_1$ and PGF$_{2\alpha}$ on the guinea pig ileum in vitro;
(E) effect on human platelet aggregation in vitro; and
(F) effect on gastric secretion in the rat;

In addition, certain of the compounds were tested for the following biological activities:

(G) effect on blood pressure and heart rate in the anesthetized cat;
(H) effect on femoral blood flow in the anesthetized dog; and
(I) effect on systolic blood pressure in the hypertensive rat

A. Evaluation of Cascade Assay Effects

The smooth muscle stimulant effects of test compounds were determined simultaneously in four different tissues that are known to be reactive to naturally occurring prostaglandins. Segments of rat stomach fundus, rat colon, chick rectum and rabbit aortic strip were obtained as described by: Vane, J. R., Brit. J. Pharmacol., 12: 344 (1957); Regoli, D. and Vane, J. R., Brit. J. Pharmacol., 23: 351 (1964); Mann, M. and West, G. B., Brit. J. Pharmacol., 5: 173 (1950); and Furchgott, R. F. and Bhadrakom, R., J. Pharmacol. Exper. Ther., 108: 129 (1953). One end of each preparation was tied to the bottom of a 10 ml tissue chamber and the other to a force displacement transducer (Grass FT-03) for continuous tension recording. The stomach, colon, and rectum segments were stretched to an initial tension of 1 g, while the aortic strip was subjected to 4 g. All preparations were left undisturbed for 1 hour prior to testing. The chambers were equipped with an external jacket through which water, maintained at 40° C., was circulated. Preparations were arranged one beneath the other in descending order (aorta, stomach, colon and rectum). Provision was made for bathing the four tissues successively so that they were superfused with the same fluid (Gaddum, J. H., Brit. J. Pharmacol., 6: 321 [1953]). The bathing fluid consisted of: Krebs bicarbonate solution aerated with a mixture of 95% O$_2$ and 5% CO$_2$ and warmed at 37° C.; atropine sulphate (0.1 mcg/ml), phenoxybenzamine hydrochloride (0.1 mcg/ml), propranolol hydrochloride (3.0 mcb/ml), methysergide maleate (0.2 mcb/ml) and brompheniramine maleate (0.1 mcg/ml) were added to eliminate the possibility of smooth muscle responses being due to stimulation of cholinergic, adrenergic, serotonin or histamine receptors. The fluid was circulated by means of a roller pump and was allowed to drip over the preparations at a rate of 10 ml/minute.

Test compounds were diluted from stock solutions so as to administer quantities ranging from 0.0001 to 100,000 ng in a volume of 0.5 ml. The compounds were applied by dripping on the uppermost tissue, at intervals of 10 to 20 minutes. Maximal increases in tension after each dose were measured and the results were used to plot dose-response curves. ED$_{50}$ data (doses necessary to produce a response 50% of maximum) were then calculated graphically for each tissue. Maximum responses utilized were those elicited by PGE$_1$ in gastric and rectal tissue, by PGF$_{2\alpha}$ in colonic tissue, and by PGA$_2$ in aortic tissue.

Activity in each tissue was scored according to the following scale:

| ED$_{50}$, ng | Activity Value |
|---|---|
| >10000 | 0 |
| 1001–10000 | 1 |
| 101–1000 | 2 |
| 10–100 | 3 |
| <10 | 4 |

B. Evaluation of the Effects on the Rat Uterus in Vitro

The uterine stimulant effect of test compounds was determined in segments of uterus obtained from rats (140-160 g) pretreated subcutaneously with 1 mg/kg of diethylstilbesterol 18 hours before the experiment. The tissues were placed in 10 ml chambers filled with de-Jalon solution at 29° C., were aerated and bubbled with 95% $O_2$ and 5% $CO_2$, and were prepared for isometric recording with force displacement transducers. Preparations were stretched to an initial tension of 1 g and were left undisturbed for 30 minutes. Carbachol (1 mcg/ml) was then added to the bath and a response was recorded. After a ten minute interval the carbachol procedure was repeated. Responses to increasing concentrations of a test compound (0.001 to 10 mcg/ml with one log intervals) were then recorded every 10 minutes. Preparations were washed four times after each response. All doses of compounds were administered in a 0.1 ml volume. Because it has been observed that the magnitude of the second response to carbachol (approximately 10% greater than the first) is close to the maximal response of the tissue, such value was taken as a measure of the sensitivity of a particular segment. Responses to each concentration of the test compound were expressed in terms of percentage of the second response to carbachol and the $ED_{50}$ (dose producing a response 50% that of carbachol) was calculated graphically.

Activity was scored according to the following scale:

| $ED_{50}$ (mcg/ml) | Activity Value |
|---|---|
| >10 | 0 |
| 1.001-10 | 1 |
| 0.101-1.0 | 2 |
| 0.01-0.1 | 3 |
| <0.01 | 4 |

C. Evaluation of the Effects on the Guinea Pig Trachea in Vitro

A male guinea pig weighing 200-500 g was killed by a blow on the head. A 20 mm length of the trachea was dissected from the animal, transferred to a petri dish containing Krebs' solution (aerated with 95% $O_2$ and 5% $CO_2$ at 37° C.), and cut longitudinally opposite the tracheal muscle. The tissue was then cut transversely three quarters of the distance across, a second cut in the opposite direction (again three quarters of the distance across the tissue) was made and the procedure was continued for the whole tissue. The ends of the trachea were pulled to form a zig-zig shaped strip. The tracheal strip used in the experiment was approximately 30 mm when extended under 0.25-0.5 g load in the tissue bath. Cotton thread was tied to one end of the tissue, and linen thread to the other. It was attached via the linen thread to a glass hook in a 5 ml isolated tissue bath containing Krebs' solution (37° C., aerated with a mixture of 95% $O_2$ and 5% $CO_2$). The opposite end was attached via cotton to an isotonic Harvard transducer (Model 386 Heart/Smooth Muscle Transducer, Harvard Apparatus). The load on the transducer lever was small, usually 0.3 g, with a range of 0.25-0.5 g, and the magnification high, 80 fold using an appropriate twin-channel per recorder. A minimum of thirty minutes was allowed before applying a test compound to the tissue. Test compounds were then applied (in volumes of 0.5 ml) at thirty minute intervals, being in contact with the tissue for five minutes followed by an overflow washout time of twenty seconds.

Prostaglandin $E_1$, at a bath concentration of 0.1 mcg/ml, was then tested repeatedly on two such strips, obtained from two different animals, until two responses (the values of which are recorded) differing by no more than 25% occur. A test compound was then added to the same two strips at bath concentrations of 0.01, 0.1, 1.0, and 10.0 mcg/ml and the effects of the compound were recorded. After the test compound had been evaluated at the highest concentration, $PGE_1$ was retested at 0.1 mcg/ml (and the value of the response recorded) to insure that the viability of the strips was retained during the experiment. The mean of the effects of the test compound on the two strips was then calculated for each concentration, and, based on the resulting values, an activity value was assigned as follows:

| Response | Activity Value |
|---|---|
| More relaxation at 0.01 mcg/ml than that elicited by $PGE_1$ | R4 |
| More relaxation at 0.1 mcg/ml than that elicited by $PGE_1$ | R3 |
| More relaxation at 1.0 mcg/ml than that elicited by $PGE_1$ | R2 |
| More relaxation at 10.0 mcg/ml than that elicited by $PGE_1$ | R1 |
| No effect at any concentration greater than that elicited by $PGE_1$ | 0 |
| More contraction at 10.0 mcg/ml than the degree of relaxation elicited by $PGE_1$ | C1 |
| More contraction at 1.0 mcg/ml than the degree of relaxation elicited by $PGE_1$ | C2 |
| More contraction at 0.1 mcg/ml than the degree of relaxation elicited by $PGE_1$ | C3 |
| More contraction at 0.01 mcg/ml than the degree of relaxation elicited by $PGE_1$ | C4 |

D. Evaluation of Antagonistic Effects on the Guinea Pig Ileum in Vitro

The degree and specificity of antagonism of test compounds to the smooth muscle stimulant effects of prostaglandins were assessed in segments of terminal guinea pig ileum. Preparations were placed in tissue chambers filled with Ringer-Tyrode solution at 37° C., bubbled with a mixture of 95% $O_2$ and 5% $CO_2$, and arranged for isometric recording with force displacement transducers. The segments were stretched to an initial tension of 1 g, and responses to a test concentration of acetylcholine (0.1 mcg/ml) were obtained every 5 minutes until two similar responses were observed (usually after four administrations). Responses to acetycholine (0.1 mcg/ml), $PGE_1$ (0.1 mcg/ml), $BaCl_2$ (100 mcg/ml) and $PGF_{2\alpha}$ (1 mcg/ml) were obtained (and recorded) in that order at 5 minute intervals before and after 100 seconds of incubation with 0.1 and 1.0 mcg/ml of the test compound. Any direct contractile effect of the test compound was recorded and evaluated in terms of mean values in grams of tension developed at each concentration. Responses to the different agonists observed after incubation with the test compound were expressed as percent of control responses. All drugs were administered in a volume of 0.1 ml.

Antagonism to prostaglandins was scored independently for PGE$_1$ and PGF$_{2\alpha}$ according to the following criteria:

| Response | Activity Value |
| --- | --- |
| Less than 50% blockade of PG response | 0 |
| More than 50% blockade of PG responses and more than 10% antagonism of Ach and/or BaCl$_2$, or production of direct contraction | 1 |
| More than 50% blockage of PG responses at 1 mcg/ml with less than 11% antagonism of Ach and BaCl$_2$ without production of direct contraction | 2 |

E. Evaluation of Inhibition of Human Platelet Aggregation

The ability of test compounds to inhibit platelet aggregation was determined by a modification of the turbidometric technique of Born, G. V. R. (*Nature*, 194: 927 [1962]). Blood was collected from human volunteers, who had not ingested aspirin or aspirin-containing products within the preceding two weeks, in heparinized containers and was allowed to settle for one (1) hour. The platelet rich plasma (prp) supernates were collected and pooled. Siliconized glassware was used throughout.

In a representative assay, 1.9 ml of PRP and 0.2 ml of test compound at the appropriate concentration (0.001 to 100 mc/gm), or 0.2 ml of distilled water (control procedure) were placed in sample cuvettes. The cuvettes were placed in a 37° C. incubation block for 15 minutes, and then in a spectrophotometer linked to a strip chart recorder. After 30–60 seconds, 0.2 ml of a solution, prepared by diluting a calf-skin collagen solution 1:9 with Tyrodes' Solution, was added to each cuvette. Platelet aggregation was evidenced by a decrease in optical density.

Calculation of the degree of inhibition of platelet aggregation exhibited by each concentration of test compound was accomplished according to the method of Caprino et al., (*Arzneim-Forsch.*, 23: 1277 [1973]). An ED$_{50}$ value was then determined graphically. Activity of the compounds was scored as follows:

| ED$_{50}$ (mcg/kg) | Activity Value |
| --- | --- |
| >1.0 | 0 |
| >0.1 and ≦1.0 | 1 |
| >0.01 and ≦0.1 | 2 |
| >0.001 and ≦0.01 | 3 |
| ≦0.001 | 4 |

F. Evaluation of the Effects on Gastric Secretion in the Rat

A procedure based on that described by Lipman, W. (*J. Pharm. Pharmacol.*, 21: 335 [1968]) was used to assess the influence of test compounds on gastric secretion. Rats of one sex weighing 150 to 200 g were randomly divided into groups of six animals each and fasted for 48 hours previous to the experiments, water being available ad libitum. The animals were anesthetized with ether, the abdomen opened through a midline incision, and the pylorus ligated. Test compounds were diluted from stock solution so as to administer a dose of 1.5 mg/kg in a volume equivalent to 1 ml/kg. Subcutaneous injections were applied immediately after surgery and again 2 hours later, so that a total dose of 3.0 mg/kg was administered. Dilutions were made with phosphate buffer (pH 7.38) as recommended by Lee et al. (*Prostaglandins*, 3: 29 [1973]) in order to insure adequate stability of drugs at the subcutaneous depot. Each compound was tested in one group of rats; an additional control group received only the vehicle.

Four hours after pylIric ligation the animals were killed with ether, the cardias ligated, and the stomachs removed. The volume of gastric secretion was measured and the contents centrifuged at 5000 rpm for 10 minutes. Total acid in the supernatent was titrated against a 0.1 N sodium hydroxide solution and the amount expressed in mEq.

Volume and total acid values of the treated group were compared with those of the controls of the t-test. Antisecretory activity was scored according to the following scale:

| % decrease in acidity | Activity Value |
| --- | --- |
| <26 | 0 |
| 26–50, not significant | 1 |
| 26–50, significant | 2 |
| 51–75 | 3 |
| 76–100 | 4 |

G. Evaluation of the Effects on Blood Pressure and Heart Rate in the Anesthetized Cat The acute effects of test compounds on blood pressure and heart rate were determined in cats of either sex anesthetized with a mixture of pentobarbital sodium (35 mg/kg, i.v.) and barbital sodium (100 mg/kg, i.v.). Cannulas were placed in the trachea to allow adequate spontaneous ventilation, in a femoral artery for blood pressure recording with a strain gage transducer, and in a saphenous vein for drug administration. Heart rate was recorded by means of a cardiotachometer driven by the R wave of the electrocardiogram. After a period of 10 minutes of stable recordings of blood pressure and heart rate, the test compound was administered intravenously at doses increasing from 0.01 to 10.0 mcg/kg, spaced one log and injected at 10 minute intervals. All doses were injected in a volume of 0.1 ml/kg. Modifications of blood pressure and heart rate induced by the test compound were expressed both in absolute units (mmHg and beats/minute) and as percent of values recorded immediately before administration of each dose. Biphasic responses were tabulated in the order in which they occurred. The direction of the observed changes is also noted (+ for increases, and − for decreases).

Activity of compounds in this test was judged only on the basis of the degree of hypotension observed. Thus, the ED$_{50}$ mmHg (dose decreasing blood pressure by 50 mmHg) was calculated graphically, and the compound scored according to the following scale:

| ED$_{50}$ mmHg, mcg/kg | Activity Value |
| --- | --- |
| >10.0 | 0 |
| 1.01–10.0 | 1 |
| 0.11–1.0 | 2 |
| 0.01–0.1 | 3 |
| <0.01 | 4 |

H. Evaluation of Effects on Femoral Blood Flow in the Anesthetized Dog

The peripheral vasodilator or constrictor effects of test compounds were determined in mongrel dogs of either sex, weighing between 10 and 20 kg, anesthetized intravenously with 35 mg/kg of pentobarbital sodium. An external iliac artery was dissected immediately above the femoral arch for a length of approximately 5 cm, and a previously calibarated, non-cannulating electromagnetic-flowmeter sensor with a lumen between 2.5 and 3.5 mm was placed snugly around the vessel. Cannulas were placed in a branch of the artery arising distally to the location of the flowmeter sensor for intra-arterial drug administrations, in the contralateral femoral artery for systemic blood pressure recording, and in the trachea for artificial respiration with room air. Femoral blood flow and systemic blood pressure were continuously recorded with an electromagnetic flowmeter and pressure transducer, respectively.

After an adequate control period, test compounds were injected intraarterially at one log-spaced doses ranging from 0.001 to 10 mcg, in a volume of 0.5 ml and at 5 to 10 minute intervals. Maximum changes in blood flow, as well as any variations in blood pressure, were tabulated for each dose in absolute values (ml/min. and mmHg), and the former were also expressed in percent. Those calculations were made taking as control values those existing immediately before administration of each dose. The direction of the observed change (+ for increase and − for decrease) was also noted. The dose changing blood flow by 100 ml/min ($ED_{100}$ml/min) was calculated graphically and was used for scoring activity as follows:

| $ED_{100}$ ml/min. mcg | Activity Value |
|---|---|
| >10.0 | 0 |
| 1.01–10.0 | 1 |
| 0.11–1.0 | 2 |
| 0.0.–0.1 | 3 |
| <0.01 | 4 |

I. Evaluation of the Effects on Blood Pressure in the Hypertensive Rat

The acute anithypertensive activity of test compounds was determined in rats made hypertensive by the procedure of Grollman (*Proc. Soc. Exper Biol. Med.*, 57: 102 [1944]). Female rats weighing between 60 and 100 g were anesthetized with ether, the right kidney approached through a flank retroperitoneal incision, decapsulated and tied with a figure-of-eight-ligature. The animals were left to recover and two weeks later were again anesthetized and the contralateral kidney removed. Four weeks after the second operation the rats were subjected to indirect blood pressure measurements and those showing systolic pressure values greater than 160 mmHg were selected for drug testing.

Blood pressure was measured in the tail with an inflatable occluding cuff placed at the base of the extremity and a pulse detector located distally. The cuff was inflated to approximately 300 mmHg and was slowly deflated until pulsations appeared, indicating the level of systolic pressure; diastolic pressure was not recorded by this procedure. All measurements were carried out in unanesthetized, unsedated animals maintained in a warm environment during the recording procedure and for at least 6 hours before. In all cases, three pressure readings were obtained in succession and mean values were calculated thereof.

Experiments were carried out in groups of five hypertensive rats in which systolic pressure was determined immediately before and 2, 4, 6 and 9 hours after intraperiotoneal administration of the test compound at a dose of 1 mg/kg. Drugs were diluted from stock solutions with phosphate buffer (Lee et al., *Prostaglandins*, 3: 29 [1973]), so as to inject this quantity in a volume of 1 ml/kg. Changes from control boood pressure values were calculated for each interval both in mmHg and in percent, and evaluated for significance by means of Wilcoxon's signed rank test (Wilcoxon, R. and Wilcox, R. A., "Some Rapid Approximate Statistical Procedures," Lederle Laboratories, Pearl River [1964]). Activity of the compound was scored as follows:

| Blood pressure decrease | Activity Value |
|---|---|
| Not significant at any time interval | 0 |
| Significant at one time interval | 1 |
| Significant at two time intervals | 2 |

Table D summarizes the results of the preceding assays performed on the prostaglandin analogues of the present invention.

TABLE D

SUMMARY OF ACTIVITY OF PROSTAGLANDIN ANALOGUES IV

| Assay | Cascade Stomache | Colon | Rectum | Aorta | Rat Uterus | Guinea Pig Trachea | Feline Blood Pressure, Heart Rate | Femoral Blood Flow | Blood Pressure Hypertensive Rat | Gastric Secretion | Antagonism PGE | PGF | Platelet Aggregation |
|---|---|---|---|---|---|---|---|---|---|---|---|---|---|
| Example 1 | 0 | 0 | 1 | 0 | 0 | 0 | 0 | 0 | 0 | 0 | 1 | 1 | 1 |
| Example 2 | 0 | 0 | 0 | 0 | 0 | 0 | NT | NT | NT | 0 | 0 | 0 | 1 |
| Example 3 | 0 | 0 | 0 | 0 | 0 | 0 | NT | NT | NT | 0 | 0 | 0 | 1 |
| Example 4 | 0 | 0 | 0 | 0 | 0 | 0 | NT | NT | 0 | 0 | 0 | 0 | 1 |
| Example 5 | 0 | 0 | 0 | 0 | 0 | 0 | NT | NT | NT | 0 | 0 | 0 | 1 |
| Example 6 | 0 | 0 | 0 | 0 | NT | 0 | NT | NT | NT | 0 | NT | NT | 1 |
| Example 7A | 0 | 0 | 0 | 0 | 0 | 1 | NT | NT | NT | 0 | 0 | 0 | 1 |
| Example 7B | 0 | 0 | 0 | 0 | 0 | 0 | NT | NT | NT | 0 | 0 | 0 | 1 |
| Example 8 | 0 | 0 | 0 | 0 | 0 | NT | NT | NT | NT | NT | NT | NT | 1 |
| Example 9 | 0 | 0 | 0 | 0 | 0 | 0 | NT | NT | NT | 0 | 0 | 0 | 1 |
| Example 10 | 0 | 0 | 0 | 0 | 0 | 0 | NT | NT | NT | 0 | 0 | 0 | 1 |
| Example 11 | 0 | 0 | 0 | 0 | 0 | 0 | NT | NT | NT | NT | 0 | 0 | 1 |
| Example 12 | 0 | 0 | 0 | 0 | 0 | 0 | NT | NT | NT | 0 | 0 | 0 | 1 |
| Example 13 | NT | NT | NT | NT | NT | NT | NT | NT | NT | NT | NT | NT | NT |
| Example 14 | 0 | 0 | 0 | 0 | 0 | 0 | NT | NT | NT | 0 | 0 | 0 | 1 |

NT = Not Tested

The prostaglandin analogue compounds of the present invention display a selective pharmacological profile insofar as they selectively inhibit platelet aggregation in vitro without causing the side effects elicited by the corresponding natural prostaglandins on gastric, tracheal, uterine, colonic, stomach, rectal and aortal tissues. In addition, Example 1 (TR 4412), demonstrated a specificity of antagonism to the smooth muscle stimulant effects of $PGE_1$ and $PGF_{2\alpha}$.

The compounds of the present invention are useful in a therapeutic method of inhibiting platelet aggregation in an individual for whom such therapy is indicated, by administering to that individual an amount of a compound having structure IV that is effective in inhibiting or decreasing platelet aggregation, reducing the adhesive character of platelets and removing or preventing the formation of thrombi. Indications for the use of compounds having structure IV include prevention of stroke, prevention and treatment of myocardial infarction and post-operative thrombosis, promoting of vascular grafts following surgery, and treatment of conditions such as atherosclerosis, arteriosclerosis and certain blood clotting defects due to lipemia. Indications for use of compounds IV are any conditions in which in hibition or decrease of platelet aggregation is desirable.

Example 1 (TR 4412) is additionally effective in a therapeutic method of inhibiting the smooth muscle stimulant response to $PGE_1$ and $PGF_{2\alpha}$ in an individual for whom such therapy is indicated by administering to that individual an amount of TR 4412 that is effective in inhibiting or decreasing response to $PGE_1$ and $PGF_{2\alpha}$. Indications for the use of TR 4412 are any conditions in which inhibition or decrease of smooth muscle response to $PGE_1$ and $PGF_{2\alpha}$ are desirable, such as treatment or prevention of dysmennorrhea or treatment of disorders of the eye, such as occular inflammation or possibly glaucoma.

The term "effective platelet aggregating inhibiting amount" and "effective smooth muscle stimulating inhibiting amount" and "effective occular inflammation reducing amount" or any equivalent of the terms means a dose or series of doses that will reduce or decrease these actions. Although the amount will vary from individual to individual and from indication to indication, it is easily determined by one skilled in the art without undue experimentation. The compounds may be administered by any known conventional mode of therapeutic administration such as intravenous, parenteral, buccal, rectal or oral. Dose forms for administration of the compounds can be prepared by recognized methods in the pharmaceutical sciences.

What is claimed is:

1. A compound having the formula

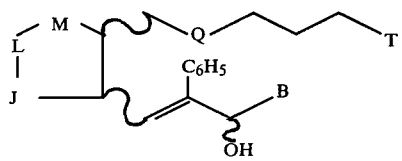

wherein:
J is selected from the group consisting of methylene, R-hydroxymethylene, S-hydroxymethylene and methine;
L is selected from the group consisting of methylene and methine with the proviso that L is methine only when J is methine;
M is selected from the group consisting of carbonyl, R-hydroxymethylene and S-hydroxymethylene;
Q is selected from the group consisting of ethylene, Z-vinylene and inter-phenylene;
T is selected from the group consisting of alkoxycarbonyl having from 2 to 3 carbon atoms inclusive, carboxyl and pharmacologically acceptable nontoxic salts; and
B is a loweralkyl having from 1 to 5 carbon atoms.

2. A compound having the formula:

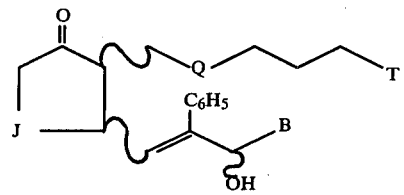

wherein:
J is selected from the group consisting of methylene and R-hydroxymethylene or S-hydroxymethylene;
Q is selected from the group consisting of ethylene, Z-vinylene and inter-phenylene;
T is selected from the group consisting of alkoxycarbonyl having from 2 to 3 carbon atoms inclusive, carboxyl and pharmacologically acceptable nontoxic salts; and
B is a loweralkyl having from 1 to 5 carbon atoms.

3. A compound according to claim 2, wherein J is R-hydroxymethylene or S-hydroxymethylene and Q is selected from the group consisting of ethylene and inter-phenylene.

4. A compound according to claim 2 and enantiomers thereof, wherein J is methylene and Q is selected from the group consisting of ethylene and inter-phenylene.

5. A compound according to claim 2 and enantiomers thereof, wherein J is methylene and Q is selected from the group consisting of ethylene and inter-o-phenylene.

6. A compound according to claim 2 wherein J is R-hydroxymethylene or S-hydroxymethylene and Q is Z-vinylene.

7. A compound according to claim 2 and enantiomers thereof, wherein J is methylene and Q is Z-vinylene.

8. A compound having the formula:

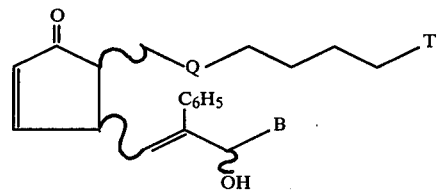

wherein:
Q is ethylene;
T is selected from the group consisting of alkoxycarbonyl having from 2 to 3 carbon atoms inclusive, carboxyl and pharmacologically acceptable nontoxic salts; and
B is a loweralkyl having from 1 to 5 carbon atoms.

9. A compound having the formula:

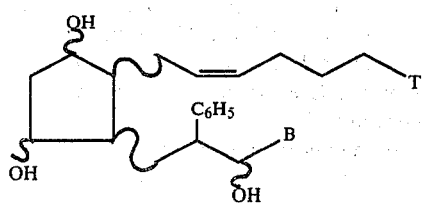

wherein:

T is selected from the group consisting of alkoxycarbonyl having from 2 to 3 carbon atoms inclusive, carboxyl and pharmacologically acceptable non-toxic salts; and B is a loweralkyl having from 1 to 5 carbon atoms.

10. Methyl 14-phenyl-11α,15S-dihydroxy-9-oxoprost-13E-en-1-oate.

11. 14-Phenyl-11α,15S-dihydroxy-9-oxoprost-13E-en-1-oic acid.

12. 14-Phenyl-11α,15R-dihydroxy-9-oxoprost-13E-en-1-oic acid.

13. Methyl 5,6,17,18,19,20-hexanor-4,7-inter-o-phenylene-14-phenyl-15S-hydroxy-9-oxo-ent-prost-13E-en-1-oate.

14. Methyl dl-14-phenyl-15R,S-hydroxy-9-oxoprost-13E-en-1-oate.

15. Methyl dl-14-phenyl-15R,S-hydroxy-9-oxoprost-13E-en-1-oic acid.

16. Ethyl 14-Phenyl-11α,15R-dihydroxy-9-oxoprosta-5Z,13E-dien-1-oate.

17. Ethyl-14-Phenyl-11α,15S-dihydroxy-9-oxoprosta-5Z,13E-dien-1-oate.

18. Methyl dl-14-phenyl-15R-hydroxy-9-oxoprosta-5,13E-dien-1-oate.

19. Methyl dl-14-phenyl-15S-hydroxy-9-oxoprosta-5Z,13E-dien-1-oate.

20. dl-14-Phenyl-15S-hydroxy-9-oxoprosta-5Z,13E-dien-1-oic acid.

21. dl-14-Phenyl-15R-hydroxy-9-oxoprosta-5Z-13E-dien-1-oic acid.

22. 14-Phenyl-15R-hydroxy-9-oxo-ent-prosta-10,13E-dien-1-oic acid.

23. 14-Phenyl-15S-hydroxy-9-oxoprosta-10,13E-dien-1-oic acid.

24. 14-Phenyl-7α,11α,15R,S-trihydroxyprosta-5Z,13E-dien-1-oic acid.

25. A therapeutic method for inhibiting platelet aggregation in an individual for whom such therapy is indicated, comprising: administering to the individual an effective platelet aggregation amount of a compound having the formula:

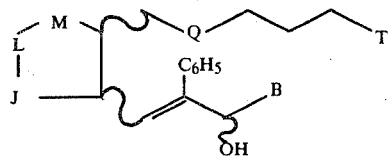

wherein:

J is selected from the group consisting of methylene, R-hydroxymethylene, S-hydroxymethylene and methine;

L is selected from the group consisting of methylene and methine with the proviso that L is methine only when J is methine;

M is selected from the group consisting of carbonyl, R-hydroxymethylene, S-hydroxymethylene;

Q is selected from the group consisting of ethylene, Z-vinylene and inter-phenylene;

T is selected from the group consisting of alkoxycarbonyl having from 2 to 3 carbon atoms inclusive, carboxyl and pharmacologically acceptable non-toxic salts; and B is a loweralkyl having from 1 to 5 carbon atoms.

26. A therapeutic method for inhibiting platelet aggregation in an individual for whom such therapy is indicated, comprising: administering to the individual an effective platelet aggregating amount of a compound having the formula:

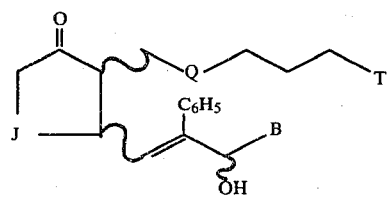

wherein:

J is selected from the group consisting of methylene and R-hydroxymethylene or S-hydroxymethylene;

Q is selected from the group consisting of ethylene, Z-vinylene and inter-phenylene;

T is selected from the group consisting of alkoxycarbonyl having from 2 to 3 carbon atoms inclusive, carboxyl and pharmacologically acceptable non-toxic salts; and B is a loweralkyl having from 1 to 5 carbon atoms.

27. A therapeutic method for inhibiting platelet aggregation in an individual for whom such therapy is indicated, comprising: administering to the individual an effective platelet aggregating amount of a compound having the formula:

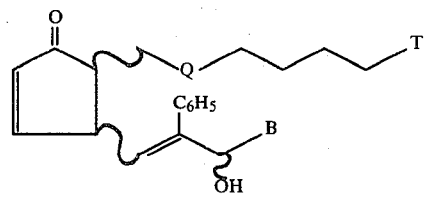

wherein:

Q is ethylene;

T is selected from the group consisting of alkoxycarbonyl having from 2 to 3 carbon atoms inclusive, carboxyl and pharmacologically acceptable non-toxic salts; and B is a loweralkyl having from 1 to 5 carbon atoms.

28. A therapeutic method for inhibiting platelet aggregation in an individual for whom such therapy is indicated, comprising: administering to the individual an effective platelet aggregating amount of a compound having the formula:

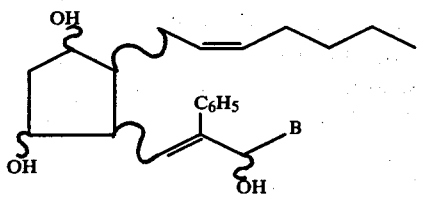

wherein:
  T is selected from the group consisting of alkoxycarbonyl having from 2 to 3 carbon atoms inclusive, carboxyl and pharmacologically acceptable non-toxic salts; and
  B is a loweralkyl having from 1 to 5 carbon atoms.

29. A therapeutic method for inhibiting platelet aggregation in an individual for whom such therapy is indicated, comprising: administering to the individual an effective platelet aggregating amount of methyl 14-phenyl-11α,15S-dihydroxy-9-oxoprost-13E-en-1-oate.

30. A therapeutic method of inhibiting the smooth muscle stimulant response to $PGE_1$ and $PGF_{2\alpha}$ in an individual for whom such therapy is indicated, comprising: administering to the individual an effective inhibiting amount of methyl 14-phenyl-11α,15S-dihydroxy-9-oxoprost-13E-en-1-oate.

31. A method for preparing a compound of the formula

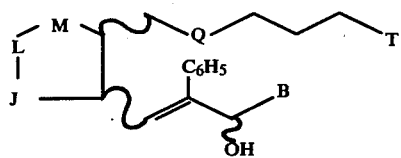

wherein:
  J is selected from the group consisting of methylene, R-hydroxymethylene, S-hydroxymethylene and methine;
  L is selected from the group consisting of methylene or methine, with the proviso that L is methine only when J is methine;
  M is selected from the group consisting of carbonyl, R-hydroxymethylene, and S-hydroxymethylene;
  Q is selected from the group consisting of ethylene, Z-vinylene and inter-phenylene;
  T is selected from the group consisting of alkoxycarbonyl having from 2 to 3 carbon atoms inclusive, carboxyl and pharmacologically acceptable non-toxic cations; and
  B is a loweralkyl of from 1 to 5 carbon atoms;
comprising:
  (a) reacting an organolithiocuprate having the formula,

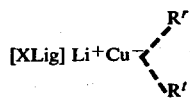

wherein:
  Lig is selected from the group consisting of tri-(dialkylamino) phosphine of 6–12 carbon atoms, trialkylphosphine having 3–13 carbon atoms, diarylphosphine, dialkylsulfide having 4–8 carbon atoms, arylsulfide, and di-(trialkylsilyl) amino having 6–12 carbon atoms;
  $R^r$ is selected from the group consisting of iodide, thiophenylate and alkyn-1-yl having 3–8 carbon atoms;
  X is an integer of the set 1 to 2;
  $R^t$ is a radical having the formula,

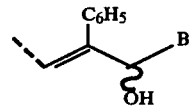

with a 2-cyclopenten-1-one having the formula,

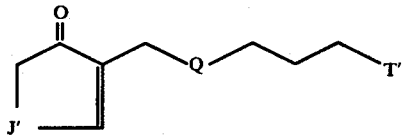

wherein:
  T' is selected from the group consisting of an alkoxycarbonyl having from 2 to 3 carbon atoms inclusive, and —$CH_2OA$;
wherein:
  A is selected from the group consisting of tetrahydropyran-2-yl, trialkylsilyl, triarylsilyl, alkoxyalkyl having 2–6 carbon atoms, or a triarylmethyl group;
in an inert solvent, under inert atmosphere, at a temperature of from about −80° C. to about +10° C. for about 0.25 to about 3 hours to form a first intermediate having the formula,

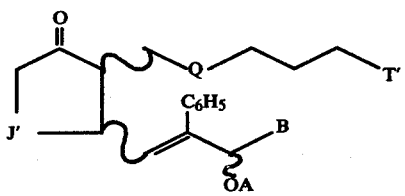

(b) reacting the first intermediate with a weak acid to obtain a first compound having the formula,

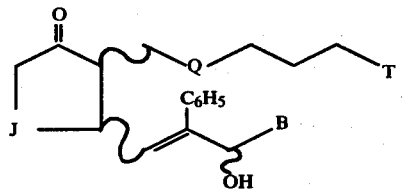

(c) when T is alkoxycarbonyl, hydrolyzing the first compound to obtain a second compound having the formula,

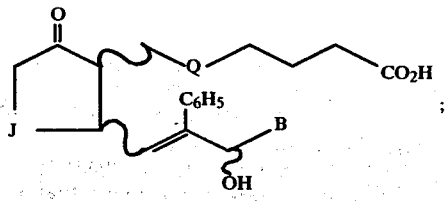

(d) when J is R-hydroxymethylene or S-hydroxymethylene, reducing the first compound to obtain a third compound having the formula,

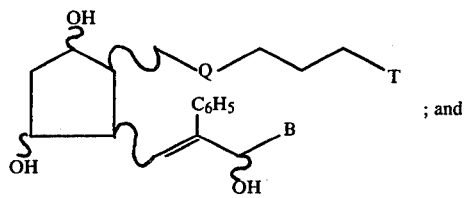 ; and (e) when J is R-hydroxymethylene or S-hydroxymethylene, dehydrating the first compound, to obtain said compound having the formula,

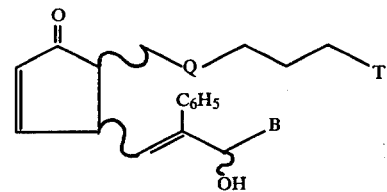

32. A method for preparing a compound having the formula,

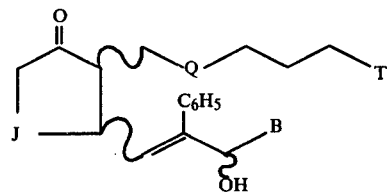

wherein:
J is selected from the group consisting of methylene and R-hydroxymethylene or S-hydroxymethylene;
Q is selected from the group consisting of ethylene, Z-vinylene and inter-phenylene;
T is selected from the group consisting of alkoxycarbonyl having from 2 to 3 carbon atoms inclusive, carboxyl and pharmacologically acceptable non-toxic cations; and
B is a loweralkyl having from 1 to 5 carbon atoms;
comprising:
(a) reacting an organolithiocuprate having the formula,

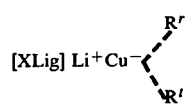

wherein:
Lig is selected from the group consisting of tri-(dialkylamino) phosphine of 6–12 carbon atoms, trialkylphosphine having 3–13 carbon atoms, diarylphosphine, dialkylsulfide having 4–8 carbon atoms, arylsulfide, and di-(trialkylsilyl) amino havng 6–12 carbon atoms;
$R^r$ is selected from the group consisting of iodide, thiophenylate and alkyn-1-yl having 3–8 carbon atoms;
X is an integer of the set 1 to 2;
$R^t$ is a radical having the formula

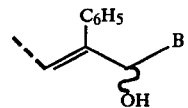

with a 2-cyclopenten-1-one having the formula,

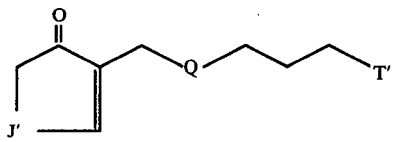

wherein:
T' is selected from the group consisting of an alkoxycarbonyl having from 2 to 3 carbon atoms inclusive, and —$CH_2OA$;
wherein:
A is selected from the group consisting of tetrahydropyran-2-yl, trialkylsilyl, triarylsilyl, alkoxyalkyl having 2–6 carbon atoms, or a triarymethyl group, in an inert solvent, under inert atmosphere, at a temperature of from about −80° C. to about +10° C. for about 0.25 to about 3 hours to form a first intermediate having the formula,

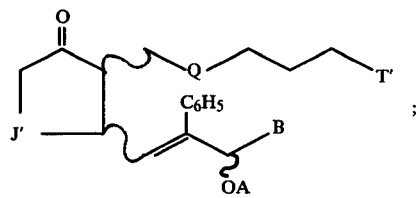

(b) reacting the first intermediate with a weak acid to obtain a first compound having the formula, wherein T is alkoxycarbonyl having from 7 to 3 carbon atoms inclusive,

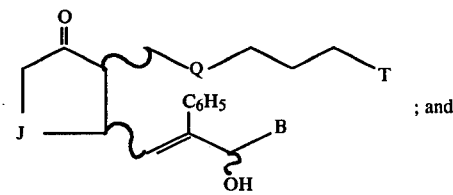 ; and (c) hydrolyzing the first compound to obtain said compound having the formula,

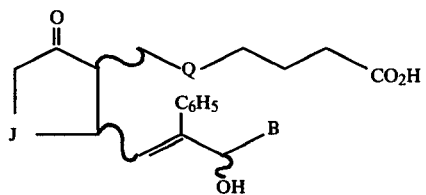

33. A method for preparing a compound having the formula,

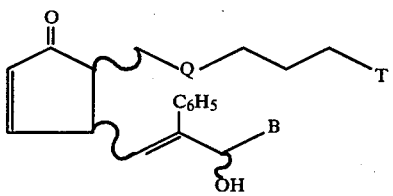

wherein:
Q ia Z-vinylene and inter-phenylene;
T is selected from the group consisting of alkoxycarbonyl having from 2 to 3 carbon atoms inclusive, carboxyl and pharmacologically acceptable non-toxic cations; and
B is a loweralkyl having from 1 to 5 carbon atoms;
comprising:
(a) reacting an organolithiocuprate having the formula,

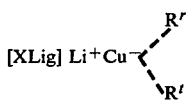

wherein:
Lig is selected from the group consisting of tri-(dialkylamino) phosphine of 6–12 carbon atoms, trialkylphosphine having 3–13 carbon atoms, diarylphosphine, dialkylsulfide having 4–8 carbon atoms, arylsulfide, and di-(trialkylsilyl) amino having 6–12 carbon atoms;
R$^r$ is selected from the group consisting of iodide, thiophenylate and alkyn-1-yl having 3–8 carbon atoms;
X is an integer of the set 1 to 2;
R$^t$ is a radical having the formula

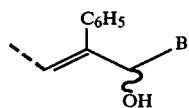

with a 2-cyclopenten-1-one having the formula,

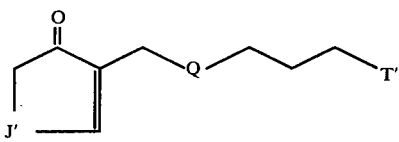

wherein:
T' is selected from the group consisting of an alkoxycarbonyl having from 2 to 3 carbon atoms, inclusive, and —CH$_2$OA;
wherein:
A is selected from the group consisting of tetrahydropyran-2-yl, trialkylsilyl, triarylsilyl, alkoxyalkyl having a 2–6 carbon atoms, or a triarymethyl group;
in an inert solvent, under inert atmosphere, at a temperature of from about −80° C. to about +10° C. for about 0.25 to about 3 hours to form a first intermediate having the formula,

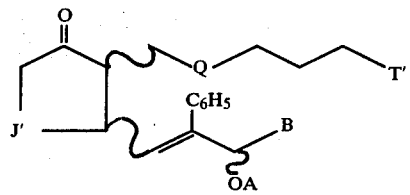

(b) reacting the first intermediate with a weak acid to obtain a first compound having the formula, wherein J is R-hydroxymethylene or S-hydroxymethylene;

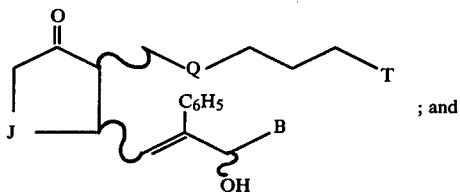
; and (c) dehydrating the first compound to obtain said compound having the formula,

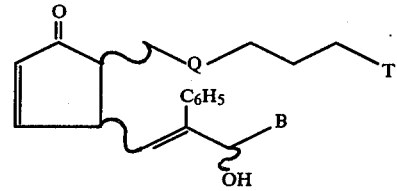

34. A method for preparing a compound having the formula,

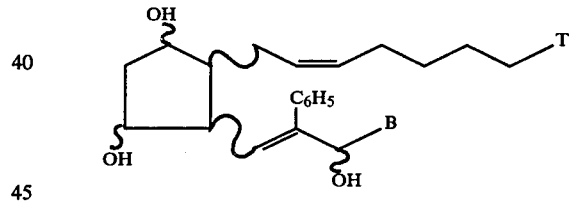

wherein:
T is selected from the group consisting of alkoyxcarbonyl having from 2 to 3 carbon atoms inclusive, carboxyl and pharmacologically acceptable non-toxic cations; and
B is loweralkyl having from 1 to 5 carbon atoms;
comprising:
(a) reacting an organolithiocuprate having the formula,

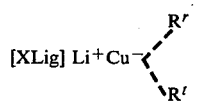

wherein:
Lig is selected from the group consisting of tri-(dialkylamino) phosphine of 6–12 carbon atoms, trialkylphosphine having 3–13 carbon atoms, diarylphosphine, dialkylsulfide having 4–8 carbon atoms, arylsulfide, and di-(trialkylsilyl) amino having 6–12 carbon atoms;

$R^r$ is selected from the group consisting of iodide, thiophenylate and alkyn-1-yl having 3–8 carbon atoms;

X is an integer of the set 1 to 2;

$R^f$ is a radical having the formula

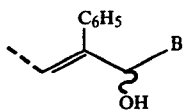

with a 2-cyclopenten-1-one having the formula,

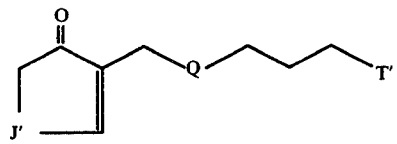

wherein:

T' is selected from the group consisting of an alkoxycarbonyl having from 2 to 3 carbon atoms inclusive, and —CH₂OA;

wherein:

A is selected from the group consisting of tetrahydropyran-2-yl, trialkylsilyl, triarylsilyl, alkoxyalkyl having a 2–6 carbon atoms, or a triarymethyl group;

in an inert solvent, under inert atmosphere, at a temperature of from about −80° C. to about +10° C. for about 0.25 to about 3 hours to form a first intermediate having the formula,

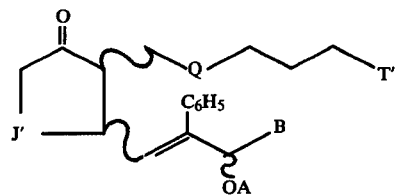

(b) reacting the first intermediate with a weak acid to obtain a first compound having the formula, wherein J is R-hydroxymethylene or S-hydroxymethylene,

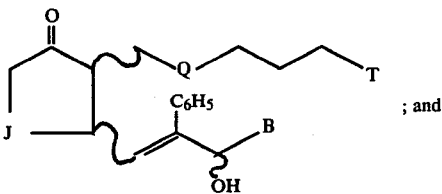

; and (c) reducing the first compound to obtain said compound having the formula,

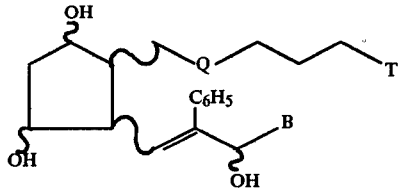

* * * * *